(12) United States Patent
Yamanaka et al.

(10) Patent No.: US 11,629,168 B2
(45) Date of Patent: Apr. 18, 2023

(54) IMMUNOGLOBULIN-BINDING PROTEIN

(71) Applicant: TOSOH CORPORATION, Yamaguchi (JP)

(72) Inventors: Naoki Yamanaka, Kanagawa (JP); Yukie Uchida, Kanagawa (JP); Yosuke Terao, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 202 days.

(21) Appl. No.: 16/762,306

(22) PCT Filed: Nov. 8, 2018

(86) PCT No.: PCT/JP2018/041551
§ 371 (c)(1),
(2) Date: May 7, 2020

(87) PCT Pub. No.: WO2019/093439
PCT Pub. Date: May 16, 2019

(65) Prior Publication Data
US 2021/0277053 A1    Sep. 9, 2021

(30) Foreign Application Priority Data

Nov. 9, 2017 (JP) ................................ 2017-216028
Mar. 9, 2018 (JP) ................................ 2018-043281
Jul. 5, 2018 (JP) ................................ 2018-128287

(51) Int. Cl.
C07K 14/31    (2006.01)
C07K 1/14    (2006.01)

(52) U.S. Cl.
CPC ................ *C07K 1/14* (2013.01); *C07K 14/31* (2013.01)

(58) Field of Classification Search
None
See application file for complete search history.

(56) References Cited

U.S. PATENT DOCUMENTS

| | | | |
|---|---|---|---|
| 2006/0194955 A1* | 8/2006 | Hober | C07K 16/065 530/388.1 |
| 2009/0299035 A1 | 12/2009 | Iwakura et al. | |
| 2010/0048876 A1 | 2/2010 | Hall et al. | |
| 2013/0046056 A1 | 2/2013 | Spector et al. | |
| 2013/0184442 A1 | 7/2013 | Hober et al. | |
| 2013/0203962 A1 | 8/2013 | Abrahmsen | |
| 2014/0005357 A1 | 1/2014 | Nakamura et al. | |
| 2014/0031522 A1 | 1/2014 | Li et al. | |
| 2014/0107315 A1 | 4/2014 | Yoshida et al. | |
| 2017/0333811 A1 | 11/2017 | Yoda et al. | |
| 2017/0334954 A1 | 11/2017 | Rodrigo et al. | |

FOREIGN PATENT DOCUMENTS

| | | |
|---|---|---|
| EP | 2557157 A1 | 2/2013 |
| JP | 2010-504754 | 2/2010 |
| JP | 2012-254981 | 12/2012 |
| JP | 2013-528567 | 7/2013 |
| JP | 2014-508118 | 4/2014 |
| WO | 2008/044692 | 4/2008 |
| WO | 2012/133349 | 10/2012 |
| WO | 2016/079033 | 5/2016 |
| WO | 2016/125811 | 8/2016 |

OTHER PUBLICATIONS

Thumbnail of Deisenhofer, J; Biochemistry (1981) 20 p. 2361-2370 from the NCBI-MMDB protein structure database.*
Partial Supplementary European Search Report dated Jul. 16, 2021, issued in corresponding EP App. No. 18875049.1.
Minakuchi et al., "Remarkable Alkaline Stability of an Engineered Protein A as Immunoblobulin Affinity Ligand: C Domain having Only One Amino Acid Substitution," *Protein Science*, 2013, vol. 22, pp. 1230-1238.
Nilsson et al., "A synthetic IgG-binding domain based on staphylococcal protein A", Protein Engineering, vol. 1, No. 2, 1987, pp. 107-113.
Official Communication (ISR) dated Jan. 29, 2019 in International Application No. PCT/JP2018/041551.
Notification of Transmittal of Translation of the International Preliminary Report on Patentability in International Application No. PCT/JP2018/041551.

* cited by examiner

*Primary Examiner* — Fred H Reynolds
(74) *Attorney, Agent, or Firm* — Greenblum & Bernstein, P.L.C.

(57) ABSTRACT

The invention aims to provide an immunoglobulin-binding protein having improved chemical stability, especially stability against alkali. The object can be achieved by improving stability against alkali by substituting an amino acid residue(s) at a particular position(s) in an immunoglobulin-binding domain such as domain C of protein A derived from a bacterium belonging to the genus *Staphylococcus*, to another/other particular amino acid residue(s).

13 Claims, No Drawings

Specification includes a Sequence Listing.

SEQUENCE LISTING

<160> NUMBER OF SEQ ID NOS: 40

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

-continued

<210> SEQ ID NO 2
<211> LENGTH: 58
<212> TYPE: PRT
<213> ORGANISM: Artificial Sequence
<220> FEATURE:
<223> OTHER INFORMATION: Immunoglobulin-binding domain of SpA having
    Lys49Met mutation

<400> SEQUENCE: 2

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Met Lys Leu Asn Asp Ala Gln Ala Pro Lys
    50                  55

<210> SEQ ID NO 3
<211> LENGTH: 174
<212> TYPE: DNA
<213> ORGANISM: Artificial Sequence
<220> FEATURE:
<223> OTHER INFORMATION: E.coli codon

<400> SEQUENCE: 3
gcggataaca agttcaacaa agaacagcag aatgcctttt atgagattct gcatttaccg      60
aatctgaccg aagaacaacg caatggcttt atccagtcgt tgaaagacga tccaagtgtg     120
agcaaagaga ttctggcaga agccaagaaa ctcaacgatg cgcaagctcc gaaa           174

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide

<400> SEQUENCE: 4
tagccatggg cgcggataac aagttc                                           26

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide

<400> SEQUENCE: 5
ctactcgagt ttcggagctt gcgcatc                                          27

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
taatacgact cactataggg                                                  20

<210> SEQ ID NO 7
<211> LENGTH: 19
<212> TYPE: DNA

```
<213> ORGANISM: Artificial Sequence
<220> FEATURE:
<223> OTHER INFORMATION: Oligonucleotide

<400> SEQUENCE: 7
tatgctagtt attgctcag                                                    19

<210> SEQ ID NO 8
<211> LENGTH: 58
<212> TYPE: PRT
<213> ORGANISM: Artificial Sequence
<220> FEATURE:
<223> OTHER INFORMATION: SpA1(Asn21Tyr)

<400> SEQUENCE: 8

Ala Asp Asn Lys Phe Asn Lys Glu Gln Gln Asn Ala Phe Tyr Glu Ile
1               5                   10                  15

Leu His Leu Pro Tyr Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Immunoglobulin-binding domain of SpA having
      Lys58Glu mutation

<400> SEQUENCE: 9

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 10
<211> LENGTH: 174
<212> TYPE: DNA
<213> ORGANISM: Artificial Sequence
<220> FEATURE:
<223> OTHER INFORMATION: Polynucleotide encoding SpA1

<400> SEQUENCE: 10
gcggataaca agttcaacaa agaacagcag aatgcctttt atgagattct gcatttaccg      60
tatctgaccg aagaacaacg caatggcttt atccagtcgt tgaaagacga tccaagtgtg     120
agcaaagaga ttctggcaga agccaagaaa ctcaacgatg cgcaagctcc gaaa           174

<210> SEQ ID NO 11
<211> LENGTH: 58
<212> TYPE: PRT
<213> ORGANISM: Artificial Sequence
<220> FEATURE:
<223> OTHER INFORMATION: SpA'(Gly29Ala)
```

<400> SEQUENCE: 11

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 12
<211> LENGTH: 174
<212> TYPE: DNA
<213> ORGANISM: Artificial Sequence
<220> FEATURE:
<223> OTHER INFORMATION: Polynucleotide encoding SpA'

<400> SEQUENCE: 12
gcggataaca agttcaacaa agaacagcag aatgcctttt atgagattct gcatttaccg    60
aatctgaccg aagaacaacg caatgccttt atccagtcgt tgaaagacga tccaagtgtg   120
agcaaagaga ttctggcaga agccaagaaa ctcaacgatg cgcaagctcc gaaa          174

<210> SEQ ID NO 13
<211> LENGTH: 58
<212> TYPE: PRT
<213> ORGANISM: Artificial Sequence
<220> FEATURE:
<223> OTHER INFORMATION: SpA2(Lys7Glu,Asn21Tyr,Gly29Ala)

<400> SEQUENCE: 13

Ala Asp Asn Lys Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 14
<211> LENGTH: 174
<212> TYPE: DNA
<213> ORGANISM: Artificial Sequence
<220> FEATURE:
<223> OTHER INFORMATION: Polynucleotide encoding SpA2

<400> SEQUENCE: 14
gcggacaaca aattcaacga agaacagcag aatgcctttt acgagattct gcatttaccg    60
tatctgaccg aagaacaacg caatgccttt atccagagct tgaaagatga tccgagtgtg   120
tcgaaagaga ttctcgctga agcgaagaaa ctgaacgatg cacaagcgcc aaaa          174

<210> SEQ ID NO 15
<211> LENGTH: 58
<212> TYPE: PRT
<213> ORGANISM: Artificial Sequence
<220> FEATURE:
<223> OTHER INFORMATION: SpA3a(Lys7Glu,Asn21Tyr,Gly29Ala,Lys58Glu)

<400> SEQUENCE: 15

Ala Asp Asn Lys Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 16
<211> LENGTH: 174
<212> TYPE: DNA
<213> ORGANISM: Artificial Sequence
<220> FEATURE:
<223> OTHER INFORMATION: Polynucleotide encoding SpA3a

<400> SEQUENCE: 16
gcggacaaca aattcaacga agaacagcag aatgcctttt acgagattct gcatttaccg    60
tatctgaccg aagaacaacg caatgccttt atccagagct tgaaagatga tccgagtgtg   120
tcgaaagaga ttctcgctga agcgaagaaa ctgaacgatg cacaagcgcc agaa         174

<210> SEQ ID NO 17
<211> LENGTH: 58
<212> TYPE: PRT
<213> ORGANISM: Artificial Sequence
<220> FEATURE:
<223> OTHER INFORMATION: SpA4a(Lys4Arg,Lys7Glu,Asn21Tyr,Gly29Ala,
      Lys58Glu)

<400> SEQUENCE: 17

Ala Asp Asn Arg Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 18
<211> LENGTH: 174
<212> TYPE: DNA
<213> ORGANISM: Artificial Sequence
<220> FEATURE:
<223> OTHER INFORMATION: Polynucleotide encoding SpA4a

<400> SEQUENCE: 18
gcggacaatc gattcaacga agaacagcag aatgcctttt acgagattct gcatttaccg    60
tatctgaccg aagaacaacg caatgccttt atccagagct tgaaagatga tccgagtgtg   120
tcgaaagaga ttctcgctga agcgaagaaa ctgaacgatg cacaagcgcc agaa         174

<210> SEQ ID NO 19
<211> LENGTH: 58
<212> TYPE: PRT
<213> ORGANISM: Artificial Sequence
<220> FEATURE:
<223> OTHER INFORMATION: SpA5a(Lys4Arg,Lys7Glu,Asn21Tyr,Gly29Ala,
      Lys49Met,Lys58Glu)

<400> SEQUENCE: 19

Ala Asp Asn Arg Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Met Lys Leu Asn Asp Ala Gln Ala Pro Glu
    50                  55

<210> SEQ ID NO 20
<211> LENGTH: 174
<212> TYPE: DNA
<213> ORGANISM: Artificial Sequence
<220> FEATURE:
<223> OTHER INFORMATION: Polynucleotide encoding SpA5a

<400> SEQUENCE: 20
gcggacaacc gcttcaacga agaacagcag aatgcctttt acgagattct gcatttaccg      60
tatctgaccg aagaacaacg caatgccttt atccagagct tgaaagatga tccgagtgtg     120
tcgaaagaga ttctcgctga agcgatgaaa ctgaacgatg cacaagcgcc agaa           174

<210> SEQ ID NO 21
<211> LENGTH: 58
<212> TYPE: PRT
<213> ORGANISM: Artificial Sequence
<220> FEATURE:
<223> OTHER INFORMATION: SpA3b(Lys4Arg,Lys7Glu,Gly29Ala,Lys58Glu)

<400> SEQUENCE: 21

Ala Asp Asn Arg Phe Asn Glu Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 22
<211> LENGTH: 174
<212> TYPE: DNA
<213> ORGANISM: Artificial Sequence
<220> FEATURE:
<223> OTHER INFORMATION: Polynucleotide encoding SpA3b

<400> SEQUENCE: 22
gcggacaacc gcttcaacga agaacagcag aatgcctttt acgagattct gcatttaccg      60
aatctgaccg aagaacaacg caatgccttt atccagagct tgaaagatga tccgagtgtg     120
tcgaaagaga ttctcgctga agcgaagaaa ctgaacgatg cacaagcgcc agaa           174

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide

<400> SEQUENCE: 23
tagccatggg cgcggacaac aaa                                               23

-continued

<210> SEQ ID NO 24
<211> LENGTH: 26
<212> TYPE: DNA
<213> ORGANISM: Artificial Sequence
<220> FEATURE:
<223> OTHER INFORMATION: Oligonucleotide

<400> SEQUENCE: 24
tagccatggg cgcggacaat cgattc                                   26

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide

<400> SEQUENCE: 25
tagccatggg cgcggacaac cgcttcaacg aa                            32

<210> SEQ ID NO 26
<211> LENGTH: 27
<212> TYPE: DNA
<213> ORGANISM: Artificial Sequence
<220> FEATURE:
<223> OTHER INFORMATION: Oligonucleotide

<400> SEQUENCE: 26
ctactcgagt tttggcgctt gtgcatc                                  27

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide

<400> SEQUENCE: 27
ctactcgagt tctggcgctt gtgcatcgtt cag                           33

<210> SEQ ID NO 28
<211> LENGTH: 58
<212> TYPE: PRT
<213> ORGANISM: Artificial Sequence
<220> FEATURE:
<223> OTHER INFORMATION: SpA5b(Asn3Ile,Lys4Arg,Lys7Glu,Asn21Tyr,
    Gly29Ala,Lys58Glu)

<400> SEQUENCE: 28

Ala Asp Ile Arg Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 29
<211> LENGTH: 58
<212> TYPE: PRT
<213> ORGANISM: Artificial Sequence
<220> FEATURE:

<223> OTHER INFORMATION: SpA5c(Asn3Thr,Lys4Arg,Lys7Glu,Asn21Tyr,
    Gly29Ala,Lys58Glu)

<400> SEQUENCE: 29

Ala Asp Thr Arg Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 30
<211> LENGTH: 58
<212> TYPE: PRT
<213> ORGANISM: Artificial Sequence
<220> FEATURE:
<223> OTHER INFORMATION: SpA5d(Lys4Arg,Lys7Glu,Asn11Lys,Asn21Tyr,
    Gly29Ala,Lys58Glu)

<400> SEQUENCE: 30

Ala Asp Asn Arg Phe Asn Glu Glu Gln Gln Lys Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 31
<211> LENGTH: 58
<212> TYPE: PRT
<213> ORGANISM: Artificial Sequence
<220> FEATURE:
<223> OTHER INFORMATION: SpA5e(Lys4Arg,Lys7Glu,Asn11Tyr,Asn21Tyr,
    Gly29Ala,Lys58Glu)

<400> SEQUENCE: 31

Ala Asp Asn Arg Phe Asn Glu Glu Gln Gln Tyr Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 32
<211> LENGTH: 58
<212> TYPE: PRT
<213> ORGANISM: Artificial Sequence
<220> FEATURE:
<223> OTHER INFORMATION: SpA4b(Lys4Arg,Lys7Glu,Asn21Tyr,Gly29Ala,
    Lys58Val)

<400> SEQUENCE: 32

Ala Asp Asn Arg Phe Asn Glu Glu Gln Gln Asn Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Val
    50                  55

<210> SEQ ID NO 33
<211> LENGTH: 174
<212> TYPE: DNA
<213> ORGANISM: Artificial Sequence
<220> FEATURE:
<223> OTHER INFORMATION: Polynucleotide encoding SpA5d

<400> SEQUENCE: 33
gcggacaatc gattcaacga agaacagcag aaagcctttt acgagattct gcatttaccg      60
tatctgaccg aagaacaacg caatgccttt atccagagct tgaaagatga tccgagtgtg     120
tcgaaagaga ttctcgctga agcgaagaaa ctgaacgatg cacaagcgcc agaa           174

<210> SEQ ID NO 34
<211> LENGTH: 58
<212> TYPE: PRT
<213> ORGANISM: Artificial Sequence
<220> FEATURE:
<223> OTHER INFORMATION: SpA6a(Lys4Arg,Lys7Glu,Asn11Lys,Glu15Ala,
      Asn21Tyr,Gly29Ala,Lys58Glu)

<400> SEQUENCE: 34

Ala Asp Asn Arg Phe Asn Glu Glu Gln Gln Lys Ala Phe Tyr Ala Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 35
<211> LENGTH: 58
<212> TYPE: PRT
<213> ORGANISM: Artificial Sequence
<220> FEATURE:
<223> OTHER INFORMATION: SpA5f(Lys4Arg,Lys7Glu,Asn11Lys,Asn21Tyr,
      Gly29Ala,Lys58Gly)

<400> SEQUENCE: 35

Ala Asp Asn Arg Phe Asn Glu Glu Gln Gln Lys Ala Phe Tyr Glu Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Gly
    50                  55

<210> SEQ ID NO 36
<211> LENGTH: 174
<212> TYPE: DNA
<213> ORGANISM: Artificial Sequence
<220> FEATURE:
<223> OTHER INFORMATION: Polynucleotide encoding SpA6a -continued

```
<400> SEQUENCE: 36
gcggacaatc gattcaacga agaacagcag aaagcctttt acgcgattct gcatttaccg    60
tatctgactg aagaacaacg caatgccttt atccagagct tgaaagatga tccgagtgtg   120
tcgaaagaga ttctcgctga agcgaagaaa ctgaacgatg cacaagcgcc agaa         174

<210> SEQ ID NO 37
<211> LENGTH: 58
<212> TYPE: PRT
<213> ORGANISM: Artificial Sequence
<220> FEATURE:
<223> OTHER INFORMATION: SpA7a(Lys4Arg,Lys7Glu,Asn11Lys,Glu15Ala,
      Asn21Tyr,Gly29Ala,Val40Ala,Lys58Glu)

<400> SEQUENCE: 37

Ala Asp Asn Arg Phe Asn Glu Glu Gln Gln Lys Ala Phe Tyr Ala Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Ala Ser Lys Glu Ile Leu Ala Glu Ala
        35                  40                  45

Lys Lys Leu Asn Asp Ala Gln Ala Pro Glu
    50                  55

<210> SEQ ID NO 38
<211> LENGTH: 58
<212> TYPE: PRT
<213> ORGANISM: Artificial Sequence
<220> FEATURE:
<223> OTHER INFORMATION: SpA7b(Asn3Ile,Lys4Arg,Lys7Glu,Asn11Lys,
      Glu15Ala,Asn21Tyr,Gly29Ala,Lys58Glu)

<400> SEQUENCE: 38

Ala Asp Ile Arg Phe Asn Glu Glu Gln Gln Lys Ala Phe Tyr Ala Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Glu
    50                  55

<210> SEQ ID NO 39
<211> LENGTH: 58
<212> TYPE: PRT
<213> ORGANISM: Artificial Sequence
<220> FEATURE:
<223> OTHER INFORMATION: SpA6b(Lys4Arg,Lys7Glu,Asn11Lys,Glu15Ala,
      Asn21Tyr,Gly29Ala,Lys58Asp)

<400> SEQUENCE: 39

Ala Asp Asn Arg Phe Asn Glu Glu Gln Gln Lys Ala Phe Tyr Ala Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp
    50                  55
```

```
<210> SEQ ID NO 40
<211> LENGTH: 58
<212> TYPE: PRT
<213> ORGANISM: Artificial Sequence
<220> FEATURE:
<223> OTHER INFORMATION: SpA6c(Lys4Arg,Lys7Glu,Asn11Lys,Glu15Ala,
      Asn21Tyr,Gly29Ala,Lys58Val)

<400> SEQUENCE: 40

Ala Asp Asn Arg Phe Asn Glu Glu Gln Gln Lys Ala Phe Tyr Ala Ile
1               5                   10                  15

Leu His Leu Pro Tyr Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Val
    50                  55
```

IMMUNOGLOBULIN-BINDING PROTEIN

SEQUENCE LISTING

The instant application contains a Sequence Listing which has been submitted electronically in ASCII format and is hereby incorporated by reference in its entirety. Said ASCII copy, created on Apr. 16, 2021, is named P59923_SL.TXT and is 18,684 bytes in size.

TECHNICAL FIELD

The present invention relates to a protein that specifically binds to immunoglobulin. More specifically, the present invention relates to an immunoglobulin-binding protein having excellent stability against alkali.

BACKGROUND ART

Antibody drugs are pharmaceuticals utilizing an antibody (immunoglobulin), which is a molecule responsible for immune functions in living organisms. By virtue of diversity of the variable region of each antibody, antibody drugs are capable of binding to target molecules with high specificity and affinity. Antibody drugs therefore have fewer side effects. Because of this, and the fact that such drugs have become applicable to a wider range of diseases in recent years, the market for antibody drugs has been rapidly expanding.

Production of an antibody drug includes a culture step and a purification step, wherein productivity in the culture step is improved by modification of antibody-producing cells and optimization of culture conditions. The purification step employs affinity chromatography for crude purification. This is followed by intermediate purification, final purification, and then virus removal before the formulation.

In the purification step, an affinity support that specifically recognizes an antibody molecule is used. As the ligand protein to be used for the support, protein A or protein G having the property of binding to the antibody (immunoglobulin) is used. In the production of the antibody drug, the affinity support is used a plurality of times for reduction of the production cost. After using the affinity support, a step of removing impurities remaining on the support is carried out. Usually, in the step of removing impurities remaining on the support, cleaning-in-place using sodium hydroxide is carried out to regenerate the affinity support. Therefore, the ligand protein needs to have sufficient chemical stability so that the antibody-binding capacity can be maintained even after this step.

Examples of the chemically stable ligand protein used for the affinity support include an alkali-stable chromatography ligand using an amino acid sequence of domain C of protein A (SpA) derived from a bacterium belonging to the genus *Staphylococcus* (Patent Document 1), and an affinity chromatography ligand composed of the same amino acid sequence as domain B, domain C, or domain Z of the protein A except for the presence of partial deletion (Patent Document 2). Further, it is known that substitution of the glycine at position 29 of domain Z to alanine stabilizes the structure (Non-patent Document 1).

PRIOR ART DOCUMENTS

Patent Documents

[Patent Document 1] Japanese Translated PCT Patent Application Laid-open No. 2010-504754
[Patent Document 2] JP 2012-254981 A Non-Patent Document

[Non-patent Document 1] Bjorn Nilsson et al., Protein Engineering, 1(2), 107-113, 1987

SUMMARY OF THE INVENTION

Problems to be Solved by the Invention

An object of the present invention is to provide an immunoglobulin-binding protein having improved stability against alkali.

Means for Solving the Problems

As a result of intensive study, the present inventors identified amino acid residues involved in improvement of the stability in domain C of protein A (SpA) derived from a bacterium belonging to the genus *Staphylococcus*, and discovered that, by substituting the amino acid residues to other specific amino acid residues, excellent stability against alkali can be achieved, thereby completing the present invention.

More specifically, the present invention includes the following modes.

[1]
An immunoglobulin-binding protein comprising an amino acid sequence which is the same as an amino acid sequence of an immunoglobulin-binding domain of protein A except that the amino acid sequence of the immunoglobulin-binding protein has at least one amino acid substitution selected from the following (1) to (8):

(1) substitution of the amino acid residue corresponding to the aspartic acid at position 2 of SEQ ID NO:1 to glutamic acid;
(2) substitution of the amino acid residue corresponding to the lysine at position 49 of SEQ ID NO:1 to methionine;
(3) substitution of the amino acid residue corresponding to the asparagine at position 21 of SEQ ID NO:1 to tyrosine;
(4) substitution of the amino acid residue corresponding to the lysine at position 58 of SEQ ID NO:1 to glutamic acid, valine, glycine, or aspartic acid;
(5) substitution of the amino acid residue corresponding to the asparagine at position 3 of SEQ ID NO:1 to isoleucine or threonine;
(6) substitution of the amino acid residue corresponding to the asparagine at position 11 of SEQ ID NO:1 to lysine or tyrosine;
(7) substitution of the amino acid residue corresponding to the glutamic acid at position 15 of SEQ ID NO:1 to alanine; and
(8) substitution of the amino acid residue corresponding to the valine at position 40 of SEQ ID NO:1 to alanine.

[2]
The immunoglobulin-binding protein which is a protein of the following (a), (b), (c), or (d):

(a) a protein containing an amino acid sequence which is the same as the amino acid sequence of SEQ ID NO:1 except that the amino acid sequence of the protein has the at least one amino acid substitution;
(b) a protein containing an amino acid sequence which is the same as the amino acid sequence of SEQ ID NO:1 except that the amino acid sequence of the protein has the at least one amino acid substitution, and also has substitution, deletion, insertion, and/or addition of one or several amino acid residues at one or several positions other than the position(s) of the at least one amino acid substitution, the protein having immunoglobulin-binding activity;

(c) a protein containing an amino acid sequence having a homology of not less than 70% with respect to the entire sequence of an amino acid sequence which is the same as the amino acid sequence of SEQ ID NO:1 except for the at least one amino acid substitution, wherein the amino acid sequence of the protein retains the at least one amino acid substitution, the protein having immunoglobulin-binding activity; or (d) a protein containing an amino acid sequence which is the same as the amino acid sequence of the protein recited in (a), (b), or (c) except that the amino acid sequence of the protein further has at least one amino acid substitution selected from the following (9) to (13):

(9) substitution of the amino acid residue corresponding to the glycine at position 29 of SEQ ID NO:1 to alanine;

(10) substitution of the amino acid residue corresponding to the lysine at position 4 of SEQ ID NO:1 to arginine;

(11) substitution of the amino acid residue corresponding to the lysine at position 7 of SEQ ID NO:1 to glutamic acid;

(12) substitution of the amino acid residue corresponding to the asparagine at position 6 of SEQ ID NO:1 to aspartic acid; and

(13) substitution of the amino acid residue corresponding to the lysine at position 42 of SEQ ID NO:1 to arginine.

[3]
The immunoglobulin-binding protein comprising an amino acid sequence which is the same as the amino acid sequence of SEQ ID NO:1 except that the amino acid sequence of the immunoglobulin-binding protein has at least the amino acid substitution(s) presented in the following (3-1) and/or (4-1):

(3-1) substitution of the asparagine at position 21 of SEQ ID NO:1 to tyrosine; and/or (4-1) substitution of the lysine at position 58 of SEQ ID NO:1 to glutamic acid.

[4]
The immunoglobulin-binding protein comprising the amino acid sequence of any of SEQ ID NOs:8, 9, 13, 15, 17, 19, and 21.

[5]
The immunoglobulin-binding protein comprising an amino acid sequence which is the same as the amino acid sequence of SEQ ID NO:17 except that the amino acid sequence of the immunoglobulin-binding protein has at least one amino acid substitution selected from the following (I) to (V):

(I) substitution of the asparagine at position 3 of SEQ ID NO:17 to isoleucine or threonine;

(II) substitution of the asparagine at position 11 of SEQ ID NO:17 to lysine or tyrosine;

(III) substitution of the glutamic acid at position 58 of SEQ ID NO:17 to valine, glycine, or aspartic acid;

(IV) substitution of the glutamic acid at position 15 of SEQ ID NO:17 to alanine; and (V) substitution of the valine at position 40 of SEQ ID NO:17 to alanine.

[6]
The immunoglobulin-binding protein comprising the amino acid sequence of any of SEQ ID NOs:28 to 32, 34, 35, and 37 to 40.

[7]
The immunoglobulin-binding protein comprising an amino acid sequence which is the same as the amino acid sequence of SEQ ID NO:1 except that the amino acid sequence of the immunoglobulin-binding protein has at least the amino acid substitution presented in the following (2-1):

(2-1) substitution of the lysine at position 49 of SEQ ID NO:1 to methionine.

[8]
The immunoglobulin-binding protein comprising the amino acid sequence of SEQ ID NO:2.

[9]
A polynucleotide encoding the immunoglobulin-binding protein.

[10]
An expression vector comprising the polynucleotide.

[11]
A transformant comprising the polynucleotide or the expression vector.

[12]
The transformant which is *Escherichia coli*.

[13]
A method of producing an immunoglobulin-binding protein, the method comprising the steps of:
culturing the transformant to allow expression of the immunoglobulin-binding protein; and
recovering the expressed protein.

[14]
An immunoglobulin adsorbent comprising:
an insoluble support; and
the immunoglobulin-binding protein immobilized on the insoluble support.

[15]
A method of separating immunoglobulin, the method comprising the steps of:
applying a solution containing immunoglobulin to a column packed with the adsorbent, to allow adsorption of the immunoglobulin to the adsorbent; and
eluting the immunoglobulin that has adsorbed to the adsorbent.

MODE FOR CARRYING OUT THE INVENTION

The present invention is described below in detail.

The immunoglobulin-binding protein of the present invention is a particular immunoglobulin-binding protein. The "immunoglobulin-binding protein" means a protein having binding capacity to immunoglobulin. Thus, the immunoglobulin-binding protein of the present invention has binding capacity to immunoglobulin. More specifically, the immunoglobulin-binding protein of the present invention may have binding capacity to the Fc region of immunoglobulin. The binding capacity to immunoglobulin is also referred to as "immunoglobulin-binding activity" or "antibody-binding activity". The immunoglobulin-binding activity can be measured by, for example, the ELISA method. The ELISA method can be carried out under, for example, the conditions described in Examples.

Examples of the immunoglobulin-binding protein of the present invention include a protein containing an amino acid sequence which is the same as an amino acid sequence of an immunoglobulin-binding domain of protein A except that the amino acid sequence of the immunoglobulin-binding protein has an amino acid substitution(s) at a particular position(s). An amino acid sequence of an immunoglobulin-binding domain of protein A having no amino acid substitution(s) at the particular position(s) is also referred to as "unmodified amino acid sequence". An amino acid sequence of an immunoglobulin-binding domain of protein A having the amino acid substitution(s) at the particular position(s) is also referred to as "modified amino acid sequence". In other words, the modified amino acid sequence may be an amino acid sequence which is the same as the unmodified amino acid sequence except that the modified amino acid sequence has the amino acid substitution(s) at the particular position(s). The immunoglobulin-binding protein of the present invention may be, for example, a protein containing an amino acid sequence which is the same as the unmodified amino acid sequence except that the amino acid sequence of the protein has the amino acid substitution(s) at the particular position(s). Further, the immunoglobulin-binding protein of the present invention may be, for example, a protein containing the modified amino acid sequence. The unmodified amino acid sequence may or may not be a naturally occurring amino acid sequence. The unmodified amino acid sequence may be modified, for example, so as to have a desired property. The unmodified amino acid sequence may have, for example, an amino acid substitution(s) other than the amino acid substitution(s) at the particular position(s).

Examples of the protein A include protein A (SpA) derived from a bacterium belonging to the genus *Staphylococcus*. Examples of the bacterium belonging to the genus *Staphylococcus* include *Staphylococcus aureus*. Examples of the immunoglobulin-binding domain include domain C, domain E, domain D, domain A, and domain B. Examples of the immunoglobulin-binding domain especially include domain C. Examples of the domain C of SpA derived from *Staphylococcus aureus* include the amino acid residues at positions 270 to 327 of GenBank No. AAA26676. The amino acid sequence of the domain C is shown in SEQ ID NO:1. Examples of the domain E of SpA derived from *Staphylococcus aureus* include the amino acid residues at positions 37 to 92 of GenBank No. AAA26676. Examples of the domain D of SpA derived from *Staphylococcus aureus* include the amino acid residues at positions 93 to 153 of GenBank No. AAA26676. Examples of the domain A of SpA derived from *Staphylococcus aureus* include the amino acid residues at positions 154 to 211 of GenBank No. AAA26676. Examples of the domain B of SpA derived from *Staphylococcus aureus* include the amino acid residues at positions 212 to 269 of GenBank No. AAA26676. In other words, specific examples of the unmodified amino acid sequence include amino acid sequences of the immunoglobulin-binding domains exemplified above, such as the amino acid sequence of SEQ ID NO:1. Specific examples of the modified amino acid sequence include an amino acid sequence which is the same as an amino acid sequence of an immunoglobulin-binding domain exemplified above such as the amino acid sequence of SEQ ID NO:1 except that the modified amino acid sequence has the amino acid substitution(s) at the particular position(s). Thus, specific examples of the immunoglobulin-binding protein of the present invention include a protein containing an amino acid sequence which is the same as an amino acid sequence of an immunoglobulin-binding domain exemplified above such as the amino acid sequence of SEQ ID NO:1 except that the amino acid sequence of the immunoglobulin-binding protein has the amino acid substitution(s) at the particular position(s). In other words, the immunoglobulin-binding protein of the present invention may be, for example, a protein containing the same amino acid sequence as an amino acid sequence of an immunoglobulin-binding domain exemplified above such as the amino acid sequence of SEQ ID NO:1 except for the presence of the amino acid substitution(s) at the particular position(s).

The fact that a protein contains an amino acid sequence is also referred to as "a protein contains amino acid residues having an amino acid sequence". The fact that a protein or an amino acid sequence has an amino acid substitution(s) is also referred to as "an amino acid substitution(s) occur(s) in a protein or an amino acid sequence". The amino acids constituting a protein or an amino acid sequence are also referred to as "amino acid residues".

More specifically, the amino acid substitution(s) at the particular position(s) is/are at least one amino acid substitution selected from Asp2Glu (this expression represents the fact that the amino acid residue corresponding to the aspartic acid at position 2 of SEQ ID NO:1 is substituted to glutamic acid; the same applies hereinafter), Lys49Met, Asn21Tyr, Lys58Glu, Lys58Val, Lys58Gly, Lys58Asp, Asn3Ile, Asn3Thr, Asn11Lys, Asn11Tyr, Glu15Ala, and Val40Ala. In other words, more specifically, the amino acid substitution(s) at the particular position(s) is/are at least one amino acid substitution selected from (1) Asp2Glu; (2) Lys49Met; (3) Asn21Tyr; (4) Lys58Glu, Lys58Val, Lys58Gly, or Lys58Asp; (5) Asn3Ile or Asn3Thr; (6) Asn11Lys or Asn11Tyr; (7) Glu15Ala; and (8) Val40Ala. The immunoglobulin-binding protein of the present invention may have, for example, one, two, three, four, five, six, seven, or eight amino acid substitution(s) selected from these amino acid substitutions. The immunoglobulin-binding protein of the present invention may have, for example, at least the amino acid substitution(s) Asp2Glu and/or Lys49Met. The immunoglobulin-binding protein of the present invention may have, for example, at least one amino acid substitution selected from Asp2Glu, Lys49Met, Asn21Tyr, and Lys58Glu. The immunoglobulin-binding protein of the present invention may have, for example, at least one amino acid substitution selected from Asp2Glu, Lys49Met, Asn21Tyr, Lys58Glu, Lys58Val, Asn3Ile, Asn3Thr, Asn11Lys, and Asn11Tyr. Among these, Asn21Tyr and Lys58Glu are amino acid substitutions with which stability against alkali can be especially improved. Thus, preferred examples of the immunoglobulin-binding protein of the present invention include immunoglobulin-binding proteins having at least the amino acid substitution Asn21Tyr or Lys58Glu. Especially preferred examples of the immunoglobulin-binding protein of the present invention include immunoglobulin-binding proteins having at least the amino acid substitutions Asn21Tyr and Lys58Glu. Preferred examples of the immunoglobulin-binding protein of the present invention also include immunoglobulin-binding proteins having at least the amino acid substitution Lys49Met.

The immunoglobulin-binding protein of the present invention may further have at least one amino acid substitution other than these. Examples of the other amino acid substitution(s) include the amino acid substitution Gly29Ala, which is known to increase structural stability (Bjorn Nilsson et al., Protein Engineering, 1(2), 107-113, 1987). Examples of the other amino acid substitution(s) also include the amino acid substitutions Lys4Arg, Lys7Glu, Asn6Asp, and Lys42Arg. Thus, examples of the modified amino acid sequence also include an amino acid sequence which is the same as an unmodified amino acid sequence exemplified above (such as the amino acid sequence of SEQ ID NO:1) except that the modified amino acid sequence has the amino acid substitution(s) at the particular position(s) and the other amino acid substitution(s) such as Gly29Ala. Thus, examples of the immunoglobulin-binding protein of the present invention also include a protein containing an amino acid sequence which is the same as an unmodified amino acid sequence exemplified above (such as the amino acid sequence of SEQ ID NO:1) except that the amino acid sequence of the immunoglobulin-binding protein has the amino acid substitution(s) at the particular position(s) and the other amino acid substitution(s) such as Gly29Ala. In other words, the immunoglobulin-binding protein of the present invention may be, for example, a protein containing the same amino acid sequence as an unmodified amino acid sequence exemplified above (such as the amino acid sequence of SEQ ID NO:1) except for the presence of the amino acid substitution(s) at the particular position(s) and the other amino acid substitution(s) such as Gly29Ala.

In cases where the immunoglobulin-binding protein of the present invention has two or more amino acid substitutions, the combination of these amino acid substitutions is not limited.

Specific examples of the combination of the amino acid substitutions include the amino acid substitutions Lys7Glu, Asn21Tyr, and Gly29Ala; the amino acid substitutions Lys7Glu, Asn21Tyr, Gly29Ala, and Lys58Glu; the amino acid substitutions Lys4Arg, Lys7Glu, Asn21Tyr, Gly29Ala, and Lys58Glu; the amino acid substitutions Lys4Arg, Lys7Glu, Asn21Tyr, Gly29Ala, Lys49Met, and Lys58Glu; the amino acid substitutions Lys4Arg, Lys7Glu, Gly29Ala, and Lys58Glu; the amino acid substitutions Asn3Ile, Lys4Arg, Lys7Glu, Asn21Tyr, Gly29Ala, and Lys58Glu; the amino acid substitutions Asn3Thr, Lys4Arg, Lys7Glu, Asn21Tyr, Gly29Ala, and Lys58Glu; the amino acid substitutions Lys4Arg, Lys7Glu, Asn11Lys, Asn21Tyr, Gly29Ala, and Lys58Glu; the amino acid substitutions Lys4Arg, Lys7Glu, Asn11Tyr, Asn21Tyr, Gly29Ala, and Lys58Glu; the amino acid substitutions Lys4Arg, Lys7Glu, Asn21Tyr, Gly29Ala, and Lys58Val; the amino acid substitutions Lys4Arg, Lys7Glu, Asn11Lys, Glu15Ala, Asn21Tyr, Gly29Ala, and Lys58Glu; the amino acid substitutions Lys4Arg, Lys7Glu, Asn11Lys, Asn21Tyr, Gly29Ala, and Lys58Gly; the amino acid substitutions Lys4Arg, Lys7Glu, Asn11Lys, Glu15Ala, Asn21Tyr, Gly29Ala, Val40Ala, and Lys58Glu; the amino acid substitutions Asn3Ile, Lys4Arg, Lys7Glu, Asn11Lys, Glu15Ala, Asn21Tyr, Gly29Ala, and Lys58Glu; the amino acid substitutions Lys4Arg, Lys7Glu, Asn11Lys, Glu15Ala, Asn21Tyr, Gly29Ala, and Lys58Asp; and the amino acid substitutions Lys4Arg, Lys7Glu, Asn11Lys, Glu15Ala, Asn21Tyr, Gly29Ala, and Lys58Val.

Thus, more specific examples of the immunoglobulin-binding protein of the present invention include the following immunoglobulin-binding proteins. These immunoglobulin-binding proteins are preferred from the viewpoint of improving stability against alkali. An immunoglobulin-binding protein containing an amino acid sequence which is the same as the amino acid sequence of SEQ ID NO:1 except that the amino acid sequence of the immunoglobulin-binding protein has the amino acid substitution Asn21Tyr (an immunoglobulin-binding protein containing the amino acid sequence of SEQ ID NO:8). An immunoglobulin-binding protein containing an amino acid sequence which is the same as the amino acid sequence of SEQ ID NO:1 except that the amino acid sequence of the immunoglobulin-binding protein has the amino acid substitution Lys58Glu (an immunoglobulin-binding protein containing the amino acid sequence of SEQ ID NO:9). An immunoglobulin-binding protein containing an amino acid sequence which is the same as the amino acid sequence of SEQ ID NO:1 except that the amino acid sequence of the immunoglobulin-binding protein has the amino acid substitutions Lys7Glu, Asn21Tyr, and Gly29Ala (an immunoglobulin-binding protein containing the amino acid sequence of SEQ ID NO:13). An immunoglobulin-binding protein containing an amino acid sequence which is the same as the amino acid sequence of SEQ ID NO:1 except that the amino acid sequence of the immunoglobulin-binding protein has the amino acid substitutions Lys7Glu, Asn21Tyr, Gly29Ala, and Lys58Glu (an immunoglobulin-binding protein containing the amino acid sequence of SEQ ID NO:15). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn21Tyr, Gly29Ala, and Lys58Glu (an immunoglobulin-binding protein containing the amino acid sequence of SEQ ID NO:17). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn21Tyr, Gly29Ala, Lys49Met, and Lys58Glu (an immunoglobulin-binding protein containing the amino acid sequence of SEQ ID NO:19). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Gly29Ala, and Lys58Glu (an immunoglobulin-binding protein containing the amino acid sequence of SEQ ID NO:21). An immunoglobulin-binding protein containing an amino acid sequence which is the same as the amino acid sequence of SEQ ID NO:1 except that the amino acid sequence of the immunoglobulin-binding protein has the amino acid substitutions Asn3Ile, Lys4Arg, Lys7Glu, Asn21Tyr, Gly29Ala, and Lys58Glu (an immunoglobulin-binding protein containing the amino acid sequence of SEQ ID NO:28). An immunoglobulin-binding protein containing an amino acid sequence which is the same as the amino acid sequence of SEQ ID NO:1 except that the amino acid sequence of the immunoglobulin-binding protein has the amino acid substitutions Asn3Thr, Lys4Arg, Lys7Glu, Asn21Tyr, Gly29Ala, and Lys58Glu (an immunoglobulin-binding protein containing the amino acid sequence of SEQ ID NO:29). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Lys, Asn21Tyr, Gly29Ala, and Lys58Glu (an immunoglobulin-binding protein containing the amino acid sequence of SEQ ID NO:30). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Tyr, Asn21Tyr, Gly29Ala, and Lys58Glu (an immunoglobulin-binding protein containing the amino acid sequence of SEQ ID NO:31). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn21Tyr, Gly29Ala, and Lys58Val (an immunoglobulin-binding protein containing the amino acid sequence of SEQ ID NO:32). An immunoglobulin-binding protein containing an amino acid sequence which is the same as the amino acid sequence of SEQ ID NO:1 except that the amino acid sequence of the immunoglobulin-binding protein has the amino acid substitution Lys49Met (an immunoglobulin-binding protein containing the amino acid sequence of SEQ ID NO:2). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Lys, Glu15Ala, Asn21Tyr, Gly29Ala, and Lys58Glu (an immunoglobulin-binding protein containing the amino acid sequence of SEQ ID NO:34). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Lys, Asn21Tyr, Gly29Ala, and Lys58Gly (an immunoglobulin-binding protein containing the amino acid sequence of SEQ ID NO:35). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Lys, Glu15Ala, Asn21Tyr, Gly29Ala, Val40Ala, and Lys58Glu (an immunoglobulin-binding protein containing the amino acid sequence of SEQ ID NO:37). An immunoglobulin-binding protein containing an amino acid sequence which is the same as the amino acid sequence of SEQ ID NO:1 except that the amino acid sequence of the immunoglobulin-binding protein has the amino acid substitutions Asn3Ile, Lys4Arg, Lys7Glu, Asn11Lys, Glu15Ala, Asn21Tyr, Gly29Ala, and Lys58Glu (an immunoglobulin-binding protein containing the amino acid sequence of SEQ ID NO:38). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Lys, Glu15Ala, Asn21Tyr, Gly29Ala, and Lys58Asp (an immunoglobulin-binding protein containing the amino acid sequence of SEQ ID NO:39). An immunoglobulin-binding protein containing an amino acid sequence which is the same as the amino acid sequence of SEQ ID NO:1 except that the amino acid sequence of the immunoglobulin-binding protein has the amino acid substitutions Lys4Arg, Lys7Glu, Asn11Lys, Glu15Ala, Asn21Tyr, Gly29Ala, and Lys58Val (an immunoglobulin-binding protein containing the amino acid sequence of SEQ ID NO:40).

Further, specific examples of the combination of amino acid substitutions include the combination of Lys4Arg, Lys7Glu, Asn21Tyr, Gly29Ala, and Lys58Glu with at least one amino acid substitution selected from the following (I) to (V):
(I) Asn3Ile or Asn3Thr;
(II) Asn11Lys, or Asn11Tyr;
(III) Lys58Val, Lys58Gly, or Lys58Asp;
(IV) Glu15Ala; and
(V) Val40Ala.

Thus, more specific examples of the immunoglobulin-binding protein of the present invention also include a protein containing an amino acid sequence which is the same as the amino acid sequence of SEQ ID NO:17 (the amino acid sequence which is the same as the amino acid sequence of SEQ ID NO:1 except for the presence of the amino acid substitutions Lys4Arg, Lys7Glu, Asn21Tyr, Gly29Ala, and Lys58Glu) except that the amino acid sequence of the protein has at least one amino acid substitution selected from the above (I) to (V). Particular examples of such a protein include an immunoglobulin-binding protein containing the amino acid sequence of any of SEQ ID NOs:28 to 32, 34, 35, and 37 to 40 described above. Here, in cases where (III) is selected, the amino acid substitution Lys58Glu contained in SEQ ID NO:17 is overwritten by an amino acid substitution such as Lys58Val, and therefore the immunoglobulin-binding protein of the present invention does not have the amino acid substitution Lys58Glu. Any of the amino acid substitutions of (I) to (V) may be read, when appropriate, using SEQ ID NO:17 as the reference sequence. Thus, for example, the "Lys58Val" mentioned herein may be read as the amino acid substitution in which the glutamic acid at position 58 of SEQ ID NO:17 is substituted to valine. The same applies to cases where other amino acid sequences are used as reference sequences.

Particular examples of the immunoglobulin-binding protein of the present invention also include a protein containing an amino acid sequence which is the same as the amino acid sequence of SEQ ID NO:17 except that the amino acid sequence of the protein has at least one amino acid substitution selected from the following (A1) to (A3):
(A1) Asn3Ile or Asn3Thr;
(A2) Asn11Lys, or Asn11Tyr;
(A3) Lys58Val.

Further, particular examples of the immunoglobulin-binding protein of the present invention also include a protein containing an amino acid sequence which is the same as the amino acid sequence of SEQ ID NO:30 (the amino acid sequence which is the same as the amino acid sequence of SEQ ID NO:1 except for the presence of the amino acid substitutions Lys4Arg, Lys7Glu, Asn11Lys, Asn21Tyr, Gly29Ala, and Lys58Glu) except that the amino acid sequence of the protein has the following amino acid substitution(s) (B1) and/or (B2):
(B1) Glu15Ala;
(B2) Lys58Gly.

Further, particular examples of the immunoglobulin-binding protein of the present invention also include a protein containing an amino acid sequence which is the same as the amino acid sequence of SEQ ID NO:34 (the amino acid sequence which is the same as the amino acid sequence of SEQ ID NO:1 except for the presence of the amino acid substitutions Lys4Arg, Lys7Glu, Asn11Lys, Glu15Ala, Asn21Tyr, Gly29Ala, and Lys58Glu) except that the amino acid sequence of the protein has at least one amino acid substitution selected from the following (C1) to (C3):
(C1) Asn3Ile;
(C2) Lys58Val or Lys58Asp;
(C3) Val40Ala.

An amino acid sequence which is the same as the amino acid sequence of SEQ ID NO:1 except for the presence of an amino acid substitution(s) exemplified above (that is, the amino acid substitution(s) at the particular position(s) described above and optionally the other amino acid substitution(s) such as Gly29Ala) is also referred to as "SEQ ID NO:1-derived substituted amino acid sequence". The SEQ ID NO:1-derived substituted amino acid sequence is, in other words, an amino acid sequence which is the same as the amino acid sequence of SEQ ID NO:1 except that an amino acid substitution(s) exemplified above (that is, the amino acid substitution(s) at the particular position(s) described above and optionally the other amino acid substitution(s) such as Gly29Ala) occurred. Further, the SEQ ID NO:1-derived substituted amino acid sequence is, in other words, an amino acid sequence which is the same as the amino acid sequence of SEQ ID NO:1 except that the SEQ ID NO:1-derived substituted amino acid sequence has an amino acid substitution(s) exemplified above (that is, the amino acid substitution(s) at the particular position(s) described above and optionally the other amino acid substitution(s) such as Gly29Ala).

Further, examples of the modified amino acid sequence also include a variant sequence of a modified amino acid sequence exemplified above (such as a SEQ ID NO:1-derived substituted amino acid sequence). Thus, examples of the immunoglobulin-binding protein of the present invention also include a protein containing a variant sequence of a modified amino acid sequence exemplified above (such as a SEQ ID NO:1-derived substituted amino acid sequence), which protein has immunoglobulin-binding activity. The following description illustrates examples of the case of a variant sequence of a SEQ ID NO:1-derived substituted amino acid sequence. The description is also applicable to variant sequences of any modified amino acid sequences.

The variant sequence of a SEQ ID NO:1-derived substituted amino acid sequence is set such that the amino acid substitution(s) at the particular position(s) remain(s) (in other words, such that the immunoglobulin-binding protein of the present invention has the amino acid substitution(s) at the particular position(s)). The variant sequence of a SEQ ID NO:1-derived substituted amino acid sequence may also be set such that the other amino acid substitution(s) such as Gly29Ala remain(s) (in other words, such that the immunoglobulin-binding protein of the present invention has the other amino acid substitution(s) such as Gly29Ala). Further, the variant sequence of a SEQ ID NO:1-derived substituted amino acid sequence may additionally have one or more amino acid substitutions not contained in the SEQ ID NO:1-derived substituted amino acid sequence, selected from, for example, the amino acid substitutions exemplified above (that is, the amino acid substitutions at the particular positions described above and optionally the other amino acid substitutions such as Gly29Ala). For example, in cases where the SEQ ID NO:1-derived substituted amino acid sequence does not have the other amino acid substitution(s) such as Gly29Ala, the variant sequence of the SEQ ID NO:1-derived substituted amino acid sequence may have the other amino acid substitution(s) such as Gly29Ala.

Examples of the variant sequence of a SEQ ID NO:1-derived substituted amino acid sequence include an amino acid sequence which is the same as the SEQ ID NO:1-derived substituted amino acid sequence except that the amino acid sequence of the variant sequence contains substitution, deletion, insertion, and/or addition of one or several amino acid residues at one or several positions. In other words, the immunoglobulin-binding protein of the present invention, as long as it has immunoglobulin-binding activity, may contain not only an amino acid substitution(s) exemplified above (that is, the amino acid substitution(s) at the particular position(s) described above and optionally the other amino acid substitution(s) such as Gly29Ala), but also substitution, deletion, insertion, and/or addition of one or several amino acid residues at one or several positions in terms of the amino acid sequence of SEQ ID NO:1. Thus, examples of the immunoglobulin-binding protein of the present invention also include a protein containing the same amino acid sequence as the amino acid sequence of SEQ ID NO:1 except for the presence of an amino acid substitution(s) exemplified above (that is, the amino acid substitution(s) at the particular position(s) described above and optionally the other amino acid substitution(s) such as Gly29Ala), and also for the presence of substitution, deletion, insertion, and/or addition of one or several amino acid residues at one or several positions, which protein has immunoglobulin-binding activity. In other words, the immunoglobulin-binding protein of the present invention may be, for example, a protein containing an amino acid sequence which is the same as the amino acid sequence of SEQ ID NO:1 except that the amino acid sequence of the protein has an amino acid substitution(s) exemplified above (that is, the amino acid substitution(s) at the particular position(s) described above and optionally the other amino acid substitution(s) such as Gly29Ala), and that the amino acid sequence of the protein also contains substitution, deletion, insertion, and/or addition of one or several amino acid residues at one or several positions, which protein has immunoglobulin-binding activity. The substitution, deletion, insertion, and/or addition of the amino acid residue(s) is/are selected such that the amino acid substitution(s) at the particular position(s) remain(s). In other words, the substitution, deletion, insertion, and/or addition of the amino acid residue(s) may occur, for example, at a position(s) other than the particular position(s) described above. Further, the substitution, deletion, insertion, and/or addition of the amino acid residue(s) may be selected such that the other amino acid substitution(s) such as Gly29Ala remain(s). In other words, the substitution, deletion, insertion, and/or addition of the amino acid residue(s) may occur, for example, at a position(s) other than the position(s) of the other amino acid substitution(s) such as Gly29Ala. Further, the substitution, deletion, insertion, and/or addition of the amino acid residue(s) may include, for example, one or more amino acid substitutions which are selected from the amino acid substitutions exemplified above and which are not contained in the SEQ ID NO:1-derived substituted amino acid sequence. More specifically, the term "one or several" means, for example, any of 1 to 30, 1 to 20, 1 to 10, 1 to 9, 1 to 8, 1 to 7, 1 to 6, 1 to 5, 1 to 4, 1 to 3, 1 to 2, and 1, depending on the position(s) of the amino acid residue(s) in the spatial structure of the protein, and on the type(s) of the amino acid residue(s). Examples of the substitution of the amino acid residue(s) include conservative substitutions, in which substitution occurs between amino acids having similar physical properties and/or chemical properties. It is known to those skilled in the art that, in cases of conservative substitutions, the protein function is generally maintained between a protein in which the substitution has occurred and a protein in which the substitution has not occurred. Examples of conservative substitutions include substitutions between glycine and alanine, between serine and proline, and between glutamic acid and alanine (Protein Structure and Function. Medical Science International, Ltd., 9, 2005). Examples of the substitution, deletion, insertion, and/or addition of the amino acid residue(s) also include those generated by naturally occurring mutations (mutants or variants), such as those based on a difference between individuals or species of the microorganism from which the protein or a gene encoding it is derived.

Examples of the variant sequence of the SEQ ID NO:1-derived substituted amino acid sequence also include amino acid sequences having high homology to the SEQ ID NO:1-derived substituted amino acid sequence. Thus, examples of the immunoglobulin-binding protein of the present invention also include a protein containing an amino acid sequence having high homology to an amino acid sequence which is the same as the amino acid sequence of SEQ ID NO:1 except for the presence of an amino acid substitution(s) exemplified above (that is, the amino acid substitution(s) at the particular position(s) described above and optionally the other amino acid substitution(s) such as Gly29Ala), which protein has immunoglobulin-binding activity. The change in the amino acid sequence within such a range of homology is selected such that the amino acid substitution(s) at the particular position(s) remain(s). In other words, the change in the amino acid sequence within such a range of homology may occur, for example, at a position(s) other than the particular position(s) described above. Further, the change in the amino acid sequence within such a range of homology may be selected such that the other amino acid substitution(s) such as Gly29Ala remain(s). In other words, the change in the amino acid sequence within such a range of homology may occur, for example, at positions other than the position(s) of the other amino acid substitution(s) such as Gly29Ala. Further, the change in the amino acid sequence within such a range of homology may include, for example, one or more amino acid substitutions which are selected from the amino acid substitutions exemplified above and which are not contained in the SEQ ID NO:1-derived substituted amino acid sequence. The "high homology" may mean a homology of not less than 70%, not less than 80%, not less than 90%, or not less than 95%. The "homology" may mean the similarity or the identity. The "homology" may especially mean the identity. The homology of the amino acid sequence can be determined using an alignment program such as BLAST. For example, the identity of the amino acid sequence may mean the identity between amino acid sequences calculated using blastp. More specifically, the identity of the amino acid sequence may also mean the identity between amino acid sequences calculated using blastp with the default parameters.

Examples of the modified amino acid sequence also include an amino acid sequence which is the same as a variant sequence exemplified above except that the modified amino acid sequence further has one or more amino acid substitutions selected from the amino acid substitutions exemplified above (that is, the amino acid substitutions at the particular positions described above and optionally the other amino acid substitutions such as Gly29Ala). For example, the modified amino acid sequence may be an amino acid sequence which is the same as a variant sequence having the amino acid substitution(s) at at least the particular position(s) described above except that the modified amino acid sequence further has the other amino acid substitution(s) such as Gly29Ala.

Examples of the unmodified amino acid sequence also include a variant sequence of an unmodified amino acid sequence exemplified above (such as the amino acid sequence of SEQ ID NO:1). Thus, examples of the modified amino acid sequence also include an amino acid sequence which is the same as a variant sequence of an unmodified amino acid sequence exemplified above (such as the amino acid sequence of SEQ ID NO:1) except that the modified amino acid sequence has an amino acid substitution(s) exemplified above (that is, the amino acid substitution(s) at the particular position(s) described above and optionally the other amino acid substitution(s) such as Gly29Ala). Thus, examples of the immunoglobulin-binding protein of the present invention also include a protein containing an amino acid sequence which is the same as a variant sequence of an unmodified amino acid sequence exemplified above (such as the amino acid sequence of SEQ ID NO:1) except that the variant sequence in the immunoglobulin-binding protein has an amino acid substitution(s) exemplified above (that is, the amino acid substitution(s) at the particular position(s) described above and optionally the other amino acid substitution(s) such as Gly29Ala), which protein has immunoglobulin-binding activity. In other words, the immunoglobulin-binding protein of the present invention may be, for example, a protein containing the same amino acid sequence as a variant sequence of an unmodified amino acid sequence exemplified above (such as the amino acid sequence of SEQ ID NO:1) except for the presence of an amino acid substitution(s) exemplified above. The following description illustrates examples of the case of a variant sequence of the amino acid sequence of SEQ ID NO:1. This description is also applicable to variant sequences of any unmodified amino acid sequences.

Examples of the variant sequence of the amino acid sequence of SEQ ID NO:1 include an amino acid sequence which is the same as the amino acid sequence of SEQ ID NO:1 except that the variant sequence contains substitution, deletion, insertion, and/or addition of one or several amino acid residues at one or several positions. Thus, examples of the immunoglobulin-binding protein of the present invention also include a protein containing an amino acid sequence which is the same as the amino acid sequence of SEQ ID NO:1 except that the amino acid sequence of the protein contains substitution, deletion, insertion, and/or addition of one or several amino acid residues at one or several positions, and that the amino acid sequence of the protein further has an amino acid substitution(s) exemplified above (that is, the amino acid substitution(s) at the particular position(s) described above and optionally the other amino acid substitution(s) such as Gly29Ala), which protein has immunoglobulin-binding activity. The substitution, deletion, insertion, and/or addition of the amino acid residue(s) may occur, for example, at a position(s) other than the particular position(s) described above. The substitution, deletion, insertion, and/or addition of the amino acid residue(s) may occur, for example, at a position(s) other than the position(s) of the other amino acid substitution(s) such as Gly29Ala.

Examples of the variant sequence of the amino acid sequence of SEQ ID NO:1 also include amino acid sequences having high homology to the amino acid sequence of SEQ ID NO:1. Thus, examples of the immunoglobulin-binding protein of the present invention also include a protein containing an amino acid sequence having high homology to the amino acid sequence of SEQ ID NO:1, wherein the amino acid sequence (amino acid sequence having high homology to the amino acid sequence of SEQ ID NO:1) has an amino acid substitution(s) exemplified above (that is, the amino acid substitution(s) at the particular position(s) described above and optionally the other amino acid substitution(s) such as Gly29Ala), which protein has immunoglobulin-binding activity. The change(s) in the amino acid residue(s) within such a range of homology may occur, for example, at a position(s) other than the particular position(s) described above. The change(s) in the amino acid residue(s) within such a range of homology may occur, for example, at a position(s) other than the position(s) of the other amino acid substitution(s) such as Gly29Ala.

The description for variant sequences of a SEQ ID NO:1-derived substituted amino acid sequence is also applicable to variant sequences of the amino acid sequence of SEQ ID NO:1.

"Amino acid at position X in the amino acid sequence of SEQ ID NO:1" means the amino acid present at the Xth position as counted from the N-terminus of the amino acid sequence of SEQ ID NO:1. "Amino acid residue corresponding to the amino acid at position X of the amino acid sequence of SEQ ID NO:1" in a certain amino acid sequence means the amino acid residue, in the certain amino acid sequence, which is placed at the same position as the Xth amino acid in the amino acid sequence of SEQ ID NO:1 in an alignment of the certain amino acid sequence with the amino acid sequence of SEQ ID NO:1. For example, in a case of the amino acid substitution Asp2Glu, "amino acid residue corresponding to the aspartic acid at position 2 of SEQ ID NO:1" in a certain amino acid sequence means the amino acid residue, in the certain amino acid sequence, which is placed at the same position as the aspartic acid at position 2 of the amino acid sequence of SEQ ID NO:1 in an alignment of the certain amino acid sequence with the amino acid sequence of SEQ ID NO:1. "Amino acid residue corresponding to the Xth amino acid in the amino acid sequence of SEQ ID NO:1" in the amino acid sequence of SEQ ID NO:1 means the Xth amino acid itself in the amino acid sequence of SEQ ID NO:1. Thus, the positions of the amino acid substitutions exemplified above (that is, the amino acid substitutions at the particular positions described above and optionally the other amino acid substitutions such as Gly29Ala) do not necessarily represent the absolute positions in the immunoglobulin-binding protein of the present invention, but represent relative positions based on the amino acid sequence of SEQ ID NO:1. That is, for example, in cases where the immunoglobulin-binding protein of the present invention contains insertion, deletion, or addition of an amino acid residue(s) in the N-terminal side relative to the positions of the amino acid substitutions exemplified above, the absolute positions of the amino acid substitutions may change in accordance therewith. The positions of the amino acid substitutions exemplified above in the immunoglobulin-binding protein of the present invention can be specified by, for example, alignment of the amino acid sequence of the immunoglobulin-binding protein of the present invention with the amino acid sequence of SEQ ID NO:1. The alignment can be carried out by, for example, using an alignment program such as BLAST. The same applies to the positions of the amino acid substitutions exemplified above in any amino acid sequences such as variant sequences of the amino acid sequence of SEQ ID NO:1. The amino acid residues before the amino acid substitutions exemplified above (that is, the amino acid substitutions at the particular positions described above and optionally the other amino acid substitutions such as Gly29Ala) represent the types of the unsubstituted amino acid residues in the amino acid sequence of SEQ ID NO:1, and may or may not be conserved in unmodified amino acid sequences other than the amino acid sequence of SEQ ID NO:1.

The immunoglobulin-binding protein of the present invention may contain only one modified amino acid sequence, or may contain a plurality of modified amino acid sequences. The immunoglobulin-binding protein of the present invention may contain, for example, not less than 2, not less than 3, not less than 4, or not less than 5 modified amino acid sequences; may contain not more than 10, not more than 7, not more than 5, not more than 4, not more than 3, or not more than 2 modified amino acid sequences; or may contain modified amino acid sequences in a consistent combination of these numbers. In cases where the immunoglobulin-binding protein of the present invention contains a plurality of modified amino acid sequences, these plurality of modified amino acid sequences may be either the same or different. The plurality of modified amino acid sequences may be linked together through, for example, an appropriate linker(s).

The immunoglobulin-binding protein of the present invention may be composed of a modified amino acid sequence, or may further contain another amino acid sequence (such as an oligopeptide). Thus, the immunoglobulin-binding protein of the present invention may further contain another amino acid sequence, for example, in the N-terminal side or the C-terminal side thereof. In other words, in the immunoglobulin-binding protein of the present invention, another amino acid sequence may be added to, for example, the N-terminal side or the C-terminal side of the modified amino acid sequence. The other amino acid sequence is not limited as long as it does not deteriorate the immunoglobulin-binding capacity or the stability of the immunoglobulin-binding protein of the present invention. For example, the type and the length of the other amino acid sequence are not limited as long as they do not deteriorate the immunoglobulin-binding capacity or the stability of the immunoglobulin-binding protein of the present invention.

The immunoglobulin-binding protein of the present invention may contain, for example, part of another immunoglobulin-binding domain as well as the immunoglobulin-binding domain selected. For example, in cases where the immunoglobulin-binding protein of the present invention contains a modified amino acid sequence of domain C, the immunoglobulin-binding protein of the present invention may further contain part of the region in the N-terminal side of domain C of protein A (domain E, domain D, domain A, and/or domain B/Z), and/or part of the region in the C-terminal side of domain C of protein A.

Further, for example, the immunoglobulin-binding protein of the present invention may contain, in its N-terminal side or C-terminal side, an oligopeptide useful for the purpose of specifically detecting or separating a target substance. Examples of such an oligopeptide include polyhistidine and polyarginine.

Further, for example, the immunoglobulin-binding protein of the present invention may contain, in its N-terminal side or C-terminal side, an oligopeptide useful for immobilizing the immunoglobulin-binding protein of the present invention on a solid phase such as a support for chromatography. Examples of such an oligopeptide include oligopeptides containing lysine or cysteine.

In cases where the immunoglobulin-binding protein of the present invention contains the above-described other amino acid sequence, for example, the immunoglobulin-binding protein of the present invention may be produced in a form already containing the other amino acid sequence, or the above-described other amino acid sequence may be separately produced and added to the protein. In cases where the immunoglobulin-binding protein of the present invention contains the above-described other amino acid sequence, the immunoglobulin-binding protein of the present invention can be typically produced by expression from a polynucleotide encoding the entire amino acid sequence of the immunoglobulin-binding protein of the present invention containing the above-described other amino acid sequence. More specifically, for example, a polynucleotide encoding the other amino acid sequence may be linked to a polynucleotide encoding the immunoglobulin-binding protein of the present invention (which, for example, does not contain the other amino acid sequence) such that the other amino acid sequence is added to the N-terminal side or the C-terminal side of the immunoglobulin-binding protein of the present invention, and then the immunoglobulin-binding protein of the present invention may be expressed. Further, for example, the other amino acid sequence may be chemically synthesized, and chemically bound to the N-terminal side or the C-terminal side of the immunoglobulin-binding protein of the present invention (which, for example, does not contain the other amino acid sequence).

The immunoglobulin-binding protein of the present invention can be produced by, for example, expression from a polynucleotide encoding the immunoglobulin-binding protein of the present invention. The polynucleotide encoding the immunoglobulin-binding protein of the present invention is also referred to as "polynucleotide of the present invention". More specifically, the polynucleotide of the present invention may be a polynucleotide containing a nucleotide sequence encoding the immunoglobulin-binding protein of the present invention.

The polynucleotide of the present invention can be obtained by, for example, a chemical synthesis method, or a DNA amplification method such as the PCR method. The DNA amplification method can be carried out using, as a template, a polynucleotide containing a nucleotide sequence to be amplified, such as a nucleotide sequence encoding the immunoglobulin-binding protein of the present invention. Examples of the polynucleotide to be used as the template include genomic DNA of an organism that expresses the immunoglobulin-binding protein of the present invention, cDNA of the immunoglobulin-binding protein of the present invention, and vectors containing the polynucleotide of the present invention. The nucleotide sequence of the polynucleotide of the present invention can be designed by, for example, conversion from the amino acid sequence of the immunoglobulin-binding protein of the present invention. In the conversion from the amino acid sequence to the nucleotide sequence, a standard codon table may be used. The conversion is preferably carried out taking into account the codon usage in the host to be transformed with the polynucleotide of the present invention. For example, in cases where the host is *Escherichia coli*, the conversion may be carried out while avoiding use of the codons AGA/AGG/CGG/CGA for arginine (Arg), ATA for isoleucine (Ile), CTA for leucine (Leu), GGA for glycine (Gly), and CCC for proline (Pro) since the usage of each of these codons is low (that is, the codons are the so-called rare codons). Analysis of the codon usage is possible by, for example, utilizing a public database (such as the Codon Usage Database provided on the website of Kazusa DNA Research Institute).

The polynucleotide of the present invention can be obtained also by, for example, introducing a mutation(s) to a polynucleotide encoding an immunoglobulin-binding protein not having the amino acid substitution(s) exemplified above (that is, the amino acid substitution(s) at the particular position(s) described above and optionally the other amino acid substitution(s) such as Gly29Ala) such that the encoded protein has the amino acid substitution(s) exemplified above. Examples of the immunoglobulin-binding protein not having the amino acid substitution(s) exemplified above include a protein containing an unmodified amino acid sequence exemplified above (such as the amino acid sequence of SEQ ID NO:1 or a variant sequence thereof). The polynucleotide encoding an immunoglobulin-binding protein not having the amino acid substitution(s) exemplified above can be obtained by, for example, a chemical synthesis method, or a DNA amplification method such as the PCR method. In cases where the immunoglobulin-binding protein of the present invention has two or more amino acid substitutions, these amino acid substitutions may be introduced, for example, simultaneously or sequentially. For example, a mutation(s) may be introduced to a polynucleotide encoding an immunoglobulin-binding protein having at least one amino acid substitution selected from the amino acid substitutions exemplified above, such that the encoded protein has at least one other amino acid substitution selected from the amino acid substitutions exemplified above. Further, the amino acid residue(s) at a certain position(s) may be modified two or more times. For example, the amino acid substitution Lys58Val may be further introduced to an immunoglobulin-binding protein already having the amino acid substitution Lys58Glu.

The mutation(s) to be introduced to the polynucleotide is/are not limited to mutations that cause the amino acid substitutions exemplified above. Any mutation(s) such as a mutation(s) for construction of a variant sequence may be introduced to use the polynucleotide as the polynucleotide of the present invention or as a material for obtaining it.

Examples of the method of the introduction of the mutation(s) to the polynucleotide include the error-prone PCR method. The reaction conditions for the error-prone PCR method are not limited as long as they are conditions under which a desired mutation(s) can be introduced to the polynucleotide. For example, a mutation(s) can be introduced to the polynucleotide by adding, to the PCR reaction liquid, the four kinds of substrate deoxynucleotides (dATP/dTTP/dCTP/dGTP) at different concentrations, and $MnCl_2$ at a concentration of 0.01 to 10 mM (preferably 0.1 to 1 mM), and then carrying out PCR. Examples of the method of introducing the mutation(s) to the polynucleotide, other than the error-prone PCR method, include methods in which an agent that acts as a mutagen is allowed to act on the polynucleotide, or the polynucleotide is irradiated with ultraviolet, to introduce the mutation(s) to the polynucleotide. Examples of the agent that acts as a mutagen include mutagenic agents commonly used by those skilled in the art, such as hydroxylamine, N-methyl-N'-nitro-N-nitrosoguanidine, nitrous acid, sulfurous acid, and hydrazine. Such methods of introducing the mutation(s) to the polynucleotide can be used not only for the introduction of the amino acid substitution(s) exemplified above, but also for construction of a variant sequence (for example, introduction of substitution, deletion, insertion, and/or addition of an amino acid residue(s), and/or changing of the amino acid sequence within the range of homology described above).

For example, the polynucleotide of the present invention may be obtained at once as the entire sequence, or may be obtained by obtaining its partial sequences and then linking the partial sequences to each other. The above description on the method of obtaining the polynucleotide of the present invention is applicable not only to cases where the entire sequence is obtained at once, but also to cases where its partial sequences are obtained.

More specifically, the immunoglobulin-binding protein of the present invention can be produced, for example, by expression of the immunoglobulin-binding protein of the present invention in a transformant having the polynucleotide of the present invention. A transformant having the polynucleotide of the present invention is also referred to as "transformant of the present invention". The transformant of the present invention can express the immunoglobulin-binding protein of the present invention based on the polynucleotide of the present invention contained therein. Thus, the transformant of the present invention is, in other words, a transformant capable of expressing the immunoglobulin-binding protein of the present invention.

The transformant of the present invention can be obtained by, for example, transforming a host using the polynucleotide of the present invention. Thus, for example, the transformant of the present invention may be a host transformed with the polynucleotide of the present invention, may be a host having the polynucleotide of the present invention, or may be a host capable of expressing the immunoglobulin-binding protein of the present invention. The host is not limited as long as the immunoglobulin-binding protein of the present invention can be expressed in cases where the host is transformed with the polynucleotide of the present invention. Examples of the host include animal cells, insect cells, and microorganisms.

Examples of the animal cells include COS cells, CHO cells, Hela cells, NIH3T3 cells, and HEK293 cells. Examples of the insect cells include Sf9 and BTI-TN-5B1-4. Examples of the microorganisms include yeasts and bacteria. Examples of the yeasts include yeasts belonging to the genus *Saccharomyces*, such as *Saccharomyces cerevisiae*; yeasts belonging to the genus *Pichia*, such as *Pichia Pastoris*; and yeasts belonging to the genus *Schizosaccharomyces*, such as *Schizosaccharomyces pombe*. Examples of the bacteria include bacteria belonging to the genus *Escherichia*, such as *Escherichia coli*. Examples of the *Escherichia coli* include the JM109 strain and the BL21 (DE3) strain. A yeast or *Escherichia coli* is preferably used as the host from the viewpoint of productivity. *Escherichia coli* is more preferably used as the host.

The polynucleotide of the present invention may be retained in the transformant of the present invention in a mode allowing its expression. More specifically, the polynucleotide of the present invention may be retained such that it is expressed under the regulation of a promoter that functions in the host. In cases where *Escherichia coli* is used as the host, examples of the promoter that functions in the host include the tip promoter, tac promoter, trc promoter, lac promoter, T7 promoter, recA promoter, and lpp promoter.

In the transformant of the present invention, the polynucleotide of the present invention may be present, for example, on a vector that self-replicates outside the genomic DNA. Thus, for example, the polynucleotide of the present invention can be introduced to the host as an expression vector containing the polynucleotide of the present invention. Thus, in one mode, the transformant of the present invention may be a transformant having an expression vector containing the polynucleotide of the present invention. The expression vector containing the polynucleotide of the present invention is also referred to as "expression vector of the present invention". The expression vector of the present invention can be obtained by, for example, inserting the polynucleotide of the present invention into an appropriate position of an expression vector. The expression vector is not limited as long as it can be stably present and is capable of replication in the host to be transformed therewith. In cases where *Escherichia coli* is used as the host, examples of the expression vector include the pET plasmid vector, pUC plasmid vector, and pTrc plasmid vector. The expression vector may contain a selection marker such as an antibiotic resistance gene. The appropriate position described above means a position where the insertion does not destroy regions involved in the replication function, selection marker, and transferability of the expression vector. In the process of inserting the polynucleotide of the present invention into the expression vector, the polynucleotide is preferably inserted in a state where it is linked to a functional polynucleotide such as a promoter required for its expression.

In the transformant of the present invention, the polynucleotide of the present invention may be introduced, for example, in the genomic DNA. The introduction of the polynucleotide of the present invention into the genomic DNA can be carried out by, for example, utilizing a gene transfer method based on homologous recombination. Examples of the gene transfer method based on homologous recombination include a method using linear DNA, such as the Red-driven integration method (Datsenko, K. A, and Wanner, B. L. Proc. Natl. Acad. Sci. USA. 97: 6640-6645 (2000)); a method using a vector containing a temperature-sensitive origin of replication; a method using a vector not having an origin of replication that functions in the host; and a transduction method using a phage.

The transformation of the host using a polynucleotide such as the expression vector of the present invention can be carried out by, for example, a method commonly used by those skilled in the art. For example, in cases where *Escherichia coli* is selected as the host, the transformation can be carried out by the competent cell method, heat shock method, electroporation method, or the like. By performing screening by an appropriate method after the transformation, the transformant of the present invention can be obtained.

Detailed information on genetic engineering methods such as expression vectors and promoters available for various microorganisms is described in, for example, "Fundamental Microbiology 8: Genetic Engineering. Kyoritsu Shuppan Co., Ltd. (1987)". These methods may be used.

In cases where the transformant of the present invention has the expression vector of the present invention, the expression vector of the present invention can be prepared from the transformant of the present invention. For example, from a culture obtained by culturing the transformant of the present invention, the expression vector of the present invention can be prepared by the alkaline extraction method, or by using a commercially available extraction kit such as the QIAprep Spin Miniprep kit (manufactured by QIAGEN).

By culturing the transformant of the present invention, the immunoglobulin-binding protein of the present invention can be expressed. By culturing the transformant of the present invention, the immunoglobulin-binding protein of the present invention can be expressed, and, by recovering the expressed protein, the immunoglobulin-binding protein of the present invention can be produced. Thus, the present invention provides a method of producing the immunoglobulin-binding protein of the present invention, the method including, for example, the steps of: culturing the transformant of the present invention to allow expression of the immunoglobulin-binding protein of the present invention; and recovering the expressed protein. The medium composition and the culture conditions may be appropriately set depending on conditions such as the type of the host and properties of the immunoglobulin-binding protein of the present invention. For example, the medium composition and the culture conditions may be set such that the host can be grown and can express the immunoglobulin-binding protein of the present invention. Examples of media that can be used therefor include media appropriately containing a carbon source, nitrogen source, inorganic salt, and/or other organic components and/or inorganic components. For example, in cases where the host is *Escherichia coli*, one preferred example of the medium is LB (Luria-Bertani) medium supplemented with necessary nutrient sources (1% (w/v) tryptone, 0.5% (w/v) yeast extract, and 1% (w/v) sodium chloride). For selective growth of the transformant of the present invention based on the presence or absence of the expression vector of the present invention introduced, the culture is preferably carried out with a medium supplemented with an antibiotic corresponding to an antibiotic resistance gene contained in the expression vector. For example, in cases where the expression vector contains a kanamycin resistance gene, the medium may be supplemented with kanamycin. The same applies to cases where the polynucleotide of the present invention is introduced in the genomic DNA. The medium may also contain one or more reducing agents selected from the group consisting of glutathione, cysteine, cystatin, thioglycolate, and dithiothreitol. The medium may also contain a reagent, such as glycine, which promotes secretion of protein from the transformant into the culture liquid. For example, in cases where the host is *Escherichia coli*, glycine is preferably added at not more than 2% (w/v) to the medium. For example, in cases where the host is *Escherichia coli*, the culture temperature may be generally 10° C. to 40° C., preferably 20° C. to 37° C., more preferably about 25° C. For example, in cases where the host is *Escherichia coli*, the pH of the medium may be pH 6.8 to pH 7.4, preferably about pH 7.0. In cases where the immunoglobulin-binding protein of the present invention is expressed under the regulation of an inducible promoter, the induction is preferably carried out so as to allow favorable expression of the immunoglobulin-binding protein of the present invention. For the induction of the expression, for example, an inducer depending on the type of the promoter may be used. Examples of the inducer may include IPTG (Isopropyl-β-D-thiogalactopyranoside). For example, in cases where the host is *Escherichia coli*, an appropriate amount of IPTG may be added when the turbidity (absorbance at 600 nm) of the culture liquid becomes about 0.5 to 1.0, and the culture may then be continued to induce expression of the immunoglobulin-binding protein of the present invention. The IPTG may be added at a concentration of, for example, 0.005 to 1.0 mM, preferably 0.01 to 0.5 mM. The induction of the expression such as IPTG induction can be carried out, for example, under conditions well known in the art.

The immunoglobulin-binding protein of the present invention can be recovered by separation from the culture by a method suitable for the mode of its expression. The "culture" means the entire culture liquid obtained by the culturing, or part thereof. The part is not limited as long as it is a part containing the immunoglobulin-binding protein of the present invention. Examples of the part include cultured cells of the transformant of the present invention, and the medium after the culturing (that is, the culture supernatant). For example, in cases where the immunoglobulin-binding protein is accumulated in the culture supernatant, the cells can be separated by a centrifugation operation, and the immunoglobulin-binding protein of the present invention can then be recovered from the resulting culture supernatant. For example, in cases where the immunoglobulin-binding protein is accumulated in the cells (including periplasm), the cells may be separated by a centrifugation operation, and then an enzyme treatment agent, surfactant, or the like may be added thereto to disrupt the cells, followed by recovering the immunoglobulin-binding protein of the present invention from the disruption product. The recovery of the immunoglobulin-binding protein of the present invention from the culture supernatant or the disrupted cells can be carried out by, for example, a known method used for separation and purification of protein. Examples of such a method include ammonium sulfate fractionation, ion-exchange chromatography, hydrophobic chromatography, affinity chromatography, gel filtration chromatography, and isoelectric precipitation.

The immunoglobulin-binding protein of the present invention can be used for, for example, separation or analysis of immunoglobulin (antibody). The immunoglobulin-binding protein of the present invention can be used by, for example, immobilization on an insoluble support. More specifically, separation or analysis of immunoglobulin (antibody) can be carried out using, for example, an immunoglobulin adsorbent comprising: an insoluble support; and the immunoglobulin-binding protein of the present invention immobilized on the insoluble support. The immunoglobulin adsorbent comprising: an insoluble support; and the immunoglobulin-binding protein of the present invention immobilized on the insoluble support; is also referred to as "immunoglobulin adsorbent of the present invention". The "separation of immunoglobulin" includes not only separation of immunoglobulin from a solution in which impurities are present, but also separation of immunoglobulins from each other based on their structures, properties, activities, and/or the like. The insoluble support is not limited. Examples of the insoluble support include supports using a polysaccharide such as agarose, alginate (alginic acid salt), carrageenan, chitin, cellulose, dextrin, dextran, or starch as a raw material; supports using a synthetic polymer such as polyvinyl alcohol, polymethacrylate, poly(2-hydroxyethyl methacrylate), or polyurethane as a raw material; and supports using a ceramic such as silica as a raw material. Among these, supports using a polysaccharide as a raw material, and supports using a synthetic polymer as a raw material, are preferred as the insoluble support. Examples of the preferred supports include polymethacrylate gels in which hydroxyl groups are introduced, such as TOYOPEARL (manufactured by Tosoh Corporation); agarose gels such as Sepharose (manufactured by GE Healthcare); and cellulose gels such as Cellufine (manufactured by JNC Corporation). The shape of the insoluble support is not limited. The insoluble support may have, for example, a form which allows packing of a column therewith. The insoluble support may be, for example, a granular matter or a nongranular matter. The insoluble support may be, for example, porous or nonporous.

The immunoglobulin-binding protein of the present invention can be immobilized on an insoluble support by, for example, covalent bonding. More specifically, for example, the immunoglobulin-binding protein of the present invention can be immobilized on an insoluble support by covalently binding the immunoglobulin-binding protein of the present invention to the insoluble support through an active group contained in the insoluble support. Thus, the insoluble support may contain an active group. For example, the insoluble support may contain the active group on the surface thereof. Examples of the active group include an N-Hydroxysuccinimide (NHS)-activated ester group, an epoxy group, a carboxyl group, a maleimide group, a haloacetyl group, a tresyl group, a formyl group, and haloacetamide. As the insoluble support containing an active group, for example, a commercially available insoluble support containing an active group may be used as it is, or an active group may be introduced to an insoluble support. Examples of commercially available insoluble supports containing an active group include TOYOPEARL AF-Epoxy-650M, TOYOPEARL AF-Tresyl-650M (these are manufactured by Tosoh Corporation), HiTrap NHS-activated HP Columns, NHS-activated Sepharose 4 Fast Flow, Epoxy-activated Sepharose 6B (these are manufactured by GE Healthcare), and SulfoLink Coupling Resin (manufactured by Thermo Fisher Scientific Inc.).

Examples of the method of introducing the active group to the surface of the support include a method in which one of two or more active sites contained in a compound is reacted with a hydroxyl group, epoxy group, carboxyl group, amino group, or the like present on the surface of the support.

Examples of the compound for introduction of an epoxy group to a hydroxyl group or an amino group present on the surface of the support include epichlorohydrin, ethanediol diglycidyl ether, butanediol diglycidyl ether, and hexanediol diglycidyl ether.

Examples of the compound for introduction of a carboxyl group to an epoxy group present on the surface of the support include 2-mercaptoacetic acid, 3-mercaptopropionic acid, 4-mercaptobutyric acid, 6-mercaptobutyric acid, glycine, 3-aminopropionic acid, 4-aminobutyric acid, and 6-aminohexanoic acid.

Examples of the compound for introduction of a maleimide group to a hydroxyl group, epoxy group, carboxyl group, or amino group present on the surface of the support include N-(ε-maleimidocaproic acid)hydrazide, N-(ε-maleimidopropionic acid)hydrazide, 4-(4-N-maleimidophenyl) acetic acid hydrazide, 2-aminomaleimide, 3-aminomaleimide, 4-aminomaleimide, 6-aminomaleimide, 1-(4-aminophenyl)maleimide, 1-β-aminophenyl)maleimide, 4-(maleimido)phenyl isocyanate, 2-maleimidoacetic acid, 3-maleimidopropionic acid, 4-maleimidobutyric acid, 6-maleimidohexanoic acid, N-(α-maleimidoacetoxy)succinimide ester, (m-maleimidobenzoyl) N-hydroxysuccinimide ester, succinimidyl-4-(maleimidomethyl)cyclohexane-1-carbonyl-(6-aminohexanoic acid), succinimidyl-4-(maleimidomethyl)cyclohexane-1-carboxylic acid, (p-maleimidobenzoyl) N-hydroxysuccinimide ester, and (m-maleimidobenzoyl) N-hydroxysuccinimide ester.

Examples of the compound for introduction of a haloacetyl group to a hydroxyl group or amino group present on the surface of the support include chloroacetic acid, bromoacetic acid, iodoacetic acid, chloroacetic chloride, bromoacetic chloride, bromoacetic bromide, chloroacetic anhydride, bromoacetic anhydride, iodoacetic anhydride, 2-(iodoacetamido)acetic acid-N-hydroxysuccinimide ester, 3-(bromoacetamido)propionic acid-N-hydroxysuccinimide ester, and 4-(iodoacetyl)aminobenzoic acid-N-hydroxysuccinimide ester.

Examples of the method of introducing the active group to the surface of the support also include a method in which ω-alkenylalkane glycidyl ether is reacted with a hydroxyl group or amino group present on the surface of the support, and then the co-alkenyl site is halogenated with a halogenating agent to cause its activation. Examples of the ω-alkenylalkane glycidyl ether include allylglycidyl ether, 3-butenylglycidyl ether, and 4-pentenylglycidyl ether. Examples of the halogenating agent include N-chlorosuccinimide, N-bromosuccinimide, and N-iodosuccinimide.

Examples of the method of introducing the active group to the surface of the support also include a method in which the active group is introduced to a carboxyl group present on the surface of the support using a condensing agent and an additive. Examples of the condensing agent include 1-ethyl-3-β-dimethylaminopropyl)carbodiimide (EDC), dicyclohexylcarbodiamide, and carbonyldiimidazole. Examples of the additive include N-hydroxysuccinimide (NHS), 4-nitrophenol, and 1-hydroxybenztriazole.

The immobilization of the immunoglobulin-binding protein of the present invention on the insoluble support can be carried out, for example, in a buffer. Examples of the buffer include acetate buffer, phosphate buffer, MES (2-morpholinoethanesulfonic acid) buffer, HEPES (4-(2-hydroxyethyl)-1-piperazineethanesulfonic acid) buffer, Tris buffer, and borate buffer. The reaction temperature for the immobilization may be appropriately set depending on, for example, conditions such as reactivity of the active group and stability of the immunoglobulin-binding protein. The reaction temperature for the immobilization may be, for example, 5° C. to 50° C., preferably 10° C. to 35° C.

The immunoglobulin adsorbent of the present invention can be used for, for example, separation of immunoglobulin (antibody) by using a column packed with the immunoglobulin adsorbent. More specifically, for example, a solution containing immunoglobulin is applied to a column packed with the immunoglobulin adsorbent of the present invention to allow adsorption of the immunoglobulin to the adsorbent, and then the immunoglobulin that has adsorbed to the adsorbent is eluted. By this, the immunoglobulin can be separated. Thus, the present invention provides, for example, a method of separating immunoglobulin, the method comprising the steps of: applying a solution containing immunoglobulin to a column packed with the immunoglobulin adsorbent of the present invention, to allow adsorption of the immunoglobulin to the adsorbent; and eluting the immunoglobulin that has adsorbed to the adsorbent. The solution containing immunoglobulin may be applied to the column using, for example, liquid transferring means such as a pump. Application of a liquid to a column is also referred to as "transfer of a liquid to a column". The solvent of the solution containing immunoglobulin may be preliminarily replaced using an appropriate buffer before the application to the column. Before the application of the solution containing immunoglobulin to the column, the column may be equilibrated using an appropriate buffer. By the equilibration of the column, for example, separation of the immunoglobulin with higher purity can be expected. Examples of the buffer used for the solvent replacement or the equilibration include phosphate buffer, acetate buffer, and MES buffer. The buffer may be further supplemented with, for example, an inorganic salt such as 10 mM to 100 mM sodium chloride. The buffer used for the solvent replacement and the buffer used for the equilibration may be either the same or different. In cases where components other than the immunoglobulin, such as impurities, are remaining in the column after passing the solution containing immunoglobulin through the column, such components may be removed from the column before the elution of the immunoglobulin that has adsorbed to the immunoglobulin adsorbent. The components other than the immunoglobulin can be removed from the column by, for example, using an appropriate buffer. To the buffer used for the removal of the components other than the immunoglobulin, for example, the description on the buffer used for the solvent replacement or for the equilibration is applicable. The immunoglobulin that has adsorbed to the immunoglobulin adsorbent can be eluted by, for example, reducing the interaction between the immunoglobulin and the ligand (the immunoglobulin-binding protein of the present invention). Examples of the means for reducing the interaction between the immunoglobulin and the ligand (the immunoglobulin-binding protein of the present invention) include lowering of the pH using a buffer, addition of a counter peptide, increasing of the temperature, and changing of the salt concentration. More specifically, the immunoglobulin that has adsorbed to the immunoglobulin adsorbent can be eluted by, for example, using an appropriate eluent. Examples of the eluent include buffers that are more acidic than the buffers used for the solvent replacement or the equilibration. Examples of such buffers include citrate buffer, glycine-HCl buffer, and acetate buffer. The pH of the eluent may be set within a range in which the function (for example, the binding capacity to antigen) of the immunoglobulin is not deteriorated.

By carrying out the separation of the immunoglobulin (antibody) in such a manner, a separated immunoglobulin, for example, is obtained. Thus, in one mode, the method of separating immunoglobulin may be a method of producing immunoglobulin, more specifically, a method of producing separated immunoglobulin. The immunoglobulin is obtained as, for example, an eluted fraction containing the immunoglobulin. Thus, a fraction containing the eluted immunoglobulin can be collected. The collection of the fraction can be carried out by, for example, an ordinary method. Examples of the method of collecting the fraction include a method in which the collection container is replaced at certain time or volume intervals, a method in which the collection container is replaced depending on the shape of the chromatogram of the eluent, and a method in which fractions are collected using an automatic fraction collector such as an auto sampler. Further, immunoglobulin can be recovered from a fraction containing the immunoglobulin. The recovery of the immunoglobulin from the fraction containing the immunoglobulin can be carried out by, for example, a known method used for separation and purification of protein.

EXAMPLES

The present invention is described below more concretely by way of Examples. However, the present invention is not limited to the Examples.

Example 1 Preparation of Immunoglobulin-Binding Protein Expression Vector (1)
From the amino acid sequence of immunoglobulin-binding protein of SEQ ID NO:1, the nucleotide sequence of SEQ ID NO:3 was designed by conversion using the *Escherichia coli*-type codons.

(2)
After synthesis of the nucleotide sequence designed in (1), PCR was used to prepare a polynucleotide containing the nucleotide sequence of SEQ ID NO:3. For the PCR, the synthesized polynucleotide was used as a template DNA, and oligonucleotides having the nucleotide sequence of

```
                                          SEQ ID NO:4
(5'-TAGCCATGGGCGCGGATAACAAGTTC-3')  or

SEQ ID NO:5
(5'-CTACTCGAGTTTCGGAGCTTGCGCATC-3')
``` were used as PCR primers, to prepare a reaction liquid having the composition shown in Table 1. The reaction liquid was then subjected to 30 cycles of reaction wherein each cycle included a first step at 98° C. for 10 seconds, a second step at 55° C. for 5 seconds, and a third step at 72° C. for 60 seconds.

TABLE 1

| Composition | Volume |
| --- | --- |
| Template DNA | 2.5 μL |
| Forward primer(10 μM) | 1 μL |
| Reverse primer(10 μM) | 1 μL |
| 5 × PrimeSTAR buffer(Takara Bio Inc.) | 10 μL |
| 2.5 mM dNTP mixture | 4 μL |
| 2.5 U/μL PrimeSTAR HS(Takara Bio Inc.) | 0.5 μL |
| H$_2$O | up to 50 μL |

(3)
The polynucleotide obtained was purified, and digested with the restriction enzymes NcoI and XhoI, followed by ligation into the expression vector pET-28a that had been preliminarily digested with the restriction enzymes NcoI and XhoI. Using the resulting ligation product, the *Escherichia coli* BL21 (DE3) strain was transformed.

(4)
The transformant obtained was cultured in LB medium supplemented with 50 μg/mL kanamycin, and then the expression vector pET-SpA was extracted using a QIAprep Spin Miniprep kit (manufactured by QIAGEN).

(5)
The polynucleotide encoding the immunoglobulin-binding protein and its vicinity in the extract obtained were subjected to cycle sequencing reaction using a Big Dye Terminator Cycle Sequencing ready Reaction kit (manufactured by Life Science), which is based on the chain terminator method. The nucleotide sequence was analyzed using an ABI Prism 3700 DNA analyzer (manufactured by Life Science), which is a fully automated DNA sequencer. In the analysis, oligonucleotides having the nucleotide sequence of

```
                                          SEQ ID NO:6
(5'-TAATACGACTCACTATAGGG-3')  or

SEQ ID NO:7
(5'-TATGCTAGTTATTGCTCAG-3')
``` were used as sequencing primers.

As a result of the sequence analysis, it could be confirmed that the expression vector pET-SpA contains a polynucleotide having the nucleotide sequence of SEQ ID NO:3 inserted therein.

Example 2 Introduction of Mutations into Immunoglobulin-Binding Protein and Preparation of Library To the polynucleotide portion (SEQ ID NO:3) encoding the immunoglobulin-binding protein inserted in the expression vector pET-SpA prepared in Example 1, mutations were randomly introduced by error-prone PCR.

(1)
Using the pET-SpA prepared in Example 1 as a template DNA, error-prone PCR was carried out. For the error-prone PCR, a reaction liquid having the composition shown in Table 2 was prepared, and the reaction liquid was heat-treated at 95° C. for 2 minutes, followed by performing 30 cycles of reaction wherein each cycle included a first step at 95° C. for 30 seconds, a second step at 50° C. for 30 seconds, and a third step at 72° C. for 90 seconds, and then finally performing heat treatment at 72° C. for 7 minutes. By the error-prone PCR, mutations were well introduced into the polynucleotide (SEQ ID NO:3) encoding the immunoglobulin-binding protein. The average mutation introduction rate was 1.15% to 1.26%.

TABLE 2

| Composition | Volume |
| --- | --- |
| Template DNA(10 ng/μL) | 1 μL |
| PCR primer(SEQ ID NO: 6)(10 μM) | 4 μL |
| PCR primer(SEQ ID NO: 7)(10 μM) | 4 μL |
| 25 mM MgCl$_2$ | 12 μL |
| 2.5 mM dNTP mixture | 8 μL |
| 10 mM MnCl$_2$ | 3 μL |
| 10 × Ex Taq buffer(Takara Bio Inc.) | 10 μL |
| GoTaq DNA polymerase(Promega KK) | 1 μL |
| H$_2$O | up to 100 μL |

(2)

The PCR product obtained was purified, and digested with the restriction enzymes NcoI and XhoI, followed by ligation into the expression vector pET-28a that had been preliminarily digested with the restriction enzymes NcoI and XhoI.

(3)

After completion of the ligation reaction, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a random mutant library.

Example 3 Screening of Alkali-Stable Immunoglobulin-Binding Proteins (Part 1)

(1)

About 1900 strains from the random mutant library (transformants) prepared in Example 2 were each inoculated into 250 μL of 2× YT liquid medium (1.6% (w/v) tryptone, 1% (w/v) yeast extract, 0.5% (w/v) sodium chloride) supplemented with 50 μg/mL kanamycin, and subjected to shake culture using 96-well deep well plates at 37° C. overnight.

(2)

Thereafter, 5 μL of the culture liquid was subcultured into 500 μL of 2× YT liquid medium supplemented with 50 μg/mL kanamycin, 0.3% glycine, and 0.05 mM IPTG (Isopropyl-β-D-thiogalactopyranoside), and further subjected to shake culture using 96-well deep well plates at 20° C. overnight.

(3)

Thereafter, a culture supernatant was obtained by a centrifugation operation, and diluted 40-fold with pure water. The diluted solution was mixed with an equal amount of 2 M NaOH, and alkali treatment was carried out at 25° C. for 16 hours. Thereafter, neutralization with 4 volumes of 1 M Tris buffer (pH 7.0) was carried out.

(4)

The antibody-binding activity of the immunoglobulin-binding protein subjected to the alkali treatment was measured by the ELISA method as described below. The antibody-binding activity of the immunoglobulin-binding protein subjected to the alkali treatment was divided by the antibody-binding activity of the immunoglobulin-binding protein without the alkali treatment, to calculate the remaining activity.

(4-1) A gamma globulin solution (manufactured by The Chemo-Sero-Therapeutic Research Institute) which is a human antibody prepared at 10 μg/mL using Tris-Buffered Saline (TBS) was dispensed into wells of 96-well microplates, followed by immobilization (4° C., 16 hours). Thereafter, blocking was carried out using bovine serum albumin (manufactured by Sigma-Aldrich) which was prepared at 1% (w/v) using TBS.

(4-2) The wells of the 96-well microplates were washed with a washing buffer (0.05 M Tris, 0.15 M NaCl, 0.05% (w/v) Tween 20 (trade name)), and then a solution containing the immunoglobulin-binding protein to be evaluated for its antibody-binding activity was added thereto, followed by reacting the immunoglobulin-binding protein with the immobilized gamma globulin (30° C., 1 hour).

(4-3) Thereafter, washing was carried out with the washing buffer, and 100 μL/well of Anti-6-His Antibody (manufactured by BETHYL LABORATORIES) diluted to 100 ng/mL was added, followed by allowing the reaction to proceed (30° C. 1 hour).

(4-4) Thereafter, washing was carried out with the washing buffer, and 50 μL/well of TMB Peroxidase Substrate (manufactured by KPL) was added. Subsequently, 50 μL/well of 1 M phosphoric acid was added to stop the reaction, and the absorbance was measured at 450 nm using a microplate reader (manufactured by TECAN).

(5)

Based on the remaining activity calculated in (4), transformants expressing an immunoglobulin-binding protein having improved alkaline stability (improved remaining activity) compared to the wild-type immunoglobulin-binding protein (having no amino acid substitution) (SEQ ID NO:1) were selected.

(6)

Each selected transformant was cultured, and an expression vector was prepared therefrom using a QIAprep Spin Miniprep kit (manufactured by QIAGEN).

(7)

The nucleotide sequence of the polynucleotide region encoding the immunoglobulin-binding protein inserted in the expression vector obtained was analyzed by the method described in Example 1(5) to identify the position of amino acid substitution.

For the immunoglobulin-binding protein expressed by each selected transformant, the position of the amino acid substitution in terms of the wild-type immunoglobulin-binding protein (having no amino acid substitution) (SEQ ID NO:1) and the remaining activity [%] after 15 hours of alkali treatment at 25° C. using 0.5 M NaOH are summarized in Table 3 and Table 4. It can be said that immunoglobulin-binding proteins in which at least any one of the amino acid substitutions Asp2Glu (this expression represents the fact that the aspartic acid at position 2 of SEQ ID NO:1 is substituted to glutamic acid; the same applies hereinafter), Lys4Arg, Lys49Met, Asn6Asp, Lys7Glu, Asn21Tyr, Lys42Arg, and Lys58Glu occurred from the amino acid sequence of SEQ ID NO:1 have improved alkaline stability compared to the wild-type immunoglobulin-binding protein (SEQ ID NO:1).

TABLE 3

| Amino acid substitution | Remaining activity[%] |
| --- | --- |
| Asp2Glu | 67 |
| Lys4Arg | 69 |
| Lys49Met | 70 |
| Wild type | 63 |

TABLE 4

| Amino acid substitution | Remaining activity[%] |
| --- | --- |
| Lys4Arg | 78 |
| Asn6Asp | 78 |
| Lys7Glu | 80 |
| Asn21Tyr | 82 |
| Lys42Arg | 74 |
| Lys58Glu | 77 |
| Wild type | 72 |

Among the immunoglobulin-binding proteins having the amino acid substitutions shown in Table 3 and Table 4, the immunoglobulin-binding protein in which the amino acid substitution Asn21Tyr occurred, which had the highest remaining activity, was named SpA1, and the expression vector containing the polynucleotide encoding SpA1 was named pET-SpA1. The amino acid sequence of SpA1 is shown in SEQ ID NO:8, and the nucleotide sequence encoding SpA1 is shown in SEQ ID NO:10.

Example 4 Preparation of Immunoglobulin-Binding Proteins Having Amino Acid Substitutions (1)
An expression vector (which was named pET-SpA') containing a polynucleotide encoding a protein (which was named SpA') which is the same as the wild-type immunoglobulin-binding protein (SEQ ID NO:1) except for the presence of an amino acid substitution Gly29Ala introduced, which contributes to structural stability (Protein Engineering, 1, 107-113; Non-patent Document 1), was prepared. The amino acid sequence of SpA' is shown in SEQ ID NO:11, and the nucleotide sequence encoding SpA' is shown in SEQ ID NO:12.

(2)
The amino acid substitutions found to be responsible for the improvement of the alkaline stability of the immunoglobulin-binding protein in Example 3 were integrated into SpA' (SEQ ID NO:11) in an attempt to further increase the stability. More specifically, the five kinds of immunoglobulin-binding proteins shown in the following (a) to (e) were designed and prepared.
(a) A protein (named SpA2) prepared by further introducing the amino acid substitutions Lys7Glu and Asn21Tyr to SpA'
(b) A protein (named SpA3a) prepared by further introducing the amino acid substitution Lys58Glu to SpA2
(c) A protein (named SpA4a) prepared by further introducing the amino acid substitution Lys4Arg to SpA3a
(d) A protein (named SpA5a) prepared by further introducing the amino acid substitution Lys49Met to SpA4a
(e) A protein (named SpA3b) prepared by further introducing the amino acid substitutions Lys4Arg, Lys7Glu, and Lys58Glu to SpA'

The methods of the preparation of the five kinds of immunoglobulin-binding proteins shown in (a) to (e) are described below.
(a) SpA2
(a-1)
Among the amino acid substitutions found to be responsible for the improvement of the alkaline stability in Example 3, Lys7Glu and Asn21Tyr were selected. These amino acid substitutions were integrated into SpA' (SEQ ID NO:11) to design the protein SpA2.
(a-2)
After synthesis of a nucleotide sequence encoding SpA2 designed in (a-1), PCR was used to prepare a polynucleotide containing the nucleotide sequence. For the PCR, the synthesized polynucleotide was used as a template DNA, and oligonucleotides having the nucleotide sequence of SEQ ID NO:23
(5'-TAGCCATGGGCGCGGACAACAAA-3') or

SEQ ID NO:26
(5'-CTACTCGAGTTTTGGCGCTTGTGCATC-3')

were used as PCR primers, to prepare a reaction liquid having the composition shown in Table 1. The reaction liquid was then heat-treated at 98° C. for 30 seconds, followed by performing 30 cycles of reaction wherein each cycle included a first step at 98° C. for 10 seconds, a second step at 55° C. for 5 seconds, and a third step at 72° C. for 60 seconds, and then finally performing heat treatment at 72° C. for 2 minutes.

(a-3)
The polynucleotide obtained was purified, and digested with the restriction enzymes NcoI and XhoI, followed by ligation into the expression vector pET-28a that had been preliminarily digested with the restriction enzymes NcoI and XhoI. Using the resulting ligation product, the *Escherichia coli* BL21 (DE3) strain was transformed.
(a-4)
The transformant obtained was cultured in LB medium supplemented with 50 μg/mL kanamycin, and then the expression vector (which was named pET-SpA2) was extracted using a QIAprep Spin Miniprep kit (manufactured by QIAGEN).
(a-5)
The nucleotide sequence of pET-SpA2 was analyzed by the same method as in Example 1(5). As a result of the sequence analysis, it could be confirmed that the expression vector pET-SpA2 contains a polynucleotide encoding SpA2 inserted therein. The amino acid sequence of SpA2 is shown in SEQ ID NO:13, and the nucleotide sequence encoding SpA2 is shown in SEQ ID NO:14.
(b) SpA3a
(b-1)
Among the amino acid substitutions found to be responsible for the improvement of the alkaline stability in Example 3, Lys7Glu, Asn21Tyr, and Lys58Glu were selected. These amino acid substitutions were integrated into SpA' (SEQ ID NO:11) to design the protein SpA3a.
(b-2)
After synthesis of a polynucleotide encoding SpA3a designed in (b-1), PCR was used to prepare a polynucleotide containing the nucleotide sequence. The PCR was carried out by the same method as in (a-2) using the synthesized polynucleotide as a template DNA, and oligonucleotides having the nucleotide sequence of SEQ ID NO:23 or

SEQ ID NO:27
(5'-CTACTCGAGTTCTGGCGCTTGTGCATCGTTCAG-3')

as PCR primers.
(b-3)
The polynucleotide obtained was purified, and digested with the restriction enzymes NcoI and XhoI, followed by ligation into the expression vector pET-28a that had been preliminarily digested with the restriction enzymes NcoI and XhoI. Using the resulting ligation product, the *Escherichia coli* BL21 (DE3) strain was transformed.
(b-4)
The transformant obtained was cultured in LB medium supplemented with 50 μg/mL kanamycin, and then the expression vector (which was named pET-SpA3a) was extracted using a QIAprep Spin Miniprep kit.
(b-5)
The nucleotide sequence of pET-SpA3a was analyzed by the same method as in Example 1(5). As a result of the sequence analysis, it could be confirmed that the expression vector pET-SpA3a contains a polynucleotide encoding SpA3a inserted therein. The amino acid sequence of SpA3a is shown in SEQ ID NO:15, and the nucleotide sequence encoding SpA3a is shown in SEQ ID NO:16.
(c) SpA4a
(c-1)
Among the amino acid substitutions found to be responsible for the improvement of the alkaline stability in Example 3, Lys4Arg, Lys7Glu, Asn21Tyr, and Lys58Glu were selected. These amino acid substitutions were integrated into SpA' (SEQ ID NO:11) to design the protein SpA4a.

(c-2)

After synthesis of a polynucleotide encoding SpA4a designed in (c-1), PCR was used to prepare a polynucleotide containing the nucleotide sequence. The PCR was carried out by the same method as in (a-2) using the synthesized polynucleotide as a template DNA, and oligonucleotides having the nucleotide sequence of

```
                                           SEQ ID NO:24
    (5'-TAGCCATGGGCGCGGACAATCGATTC-3')
``` or SEQ ID NO:27 as PCR primers.

(c-3)

The polynucleotide obtained was purified, and digested with the restriction enzymes NcoI and XhoI, followed by ligation into the expression vector pET-28a that had been preliminarily digested with the restriction enzymes NcoI and XhoI. Using the resulting ligation product, the *Escherichia coli* BL21 (DE3) strain was transformed.

(c-4)

The transformant obtained was cultured in LB medium supplemented with 50 μg/mL kanamycin, and then the expression vector (which was named pET-SpA4a) was extracted using a QIAprep Spin Miniprep kit.

(c-5)

The nucleotide sequence of pET-SpA4a was analyzed by the same method as in Example 1(5). As a result of the sequence analysis, it could be confirmed that the expression vector pET-SpA4a contains a polynucleotide encoding SpA4a inserted therein. The amino acid sequence of SpA4a is shown in SEQ ID NO:17, and the nucleotide sequence encoding SpA4a is shown in SEQ ID NO:18.

(d) SpA5a (d-1)

Among the amino acid substitutions found to be responsible for the improvement of the alkaline stability in Example 3, Lys4Arg, Lys7Glu, Asn21Tyr, Lys49Met, and Lys58Glu were selected. These amino acid substitutions were integrated into SpA' (SEQ ID NO:11) to design the protein SpA5a.

(d-2)

After synthesis of a polynucleotide encoding SpA5a designed in (d-1), PCR was used to prepare a polynucleotide containing the nucleotide sequence. The PCR was carried out by the same method as in (a-2) using the synthesized polynucleotide as a template DNA, and oligonucleotides having the nucleotide sequence of

```
                                           SEQ ID NO:25
    (5'-TAGCCATGGGCGCGGACAACCGCTTCAACGAA-3')
``` or SEQ ID NO:27 as PCR primers.

(d-3)

The polynucleotide obtained was purified, and digested with the restriction enzymes NcoI and XhoI, followed by ligation into the expression vector pET-28a that had been preliminarily digested with the restriction enzymes NcoI and XhoI. Using the resulting ligation product, the *Escherichia coli* BL21 (DE3) strain was transformed.

(d-4)

The transformant obtained was cultured in LB medium supplemented with 50 μg/mL kanamycin, and then the expression vector (which was named pET-SpA5a) was extracted using a QIAprep Spin Miniprep kit.

(d-5)

The nucleotide sequence of pET-SpA5a was analyzed by the same method as in Example 1(5). As a result of the sequence analysis, it could be confirmed that the expression vector pET-SpA5a contains a polynucleotide encoding SpA5a inserted therein. The amino acid sequence of SpA5a is shown in SEQ ID NO:19, and the nucleotide sequence encoding SpA5a is shown in SEQ ID NO:20.

(e) SpA3b (e-1)

Among the amino acid substitutions found to be responsible for the improvement of the alkaline stability in Example 3, Lys4Arg, Lys7Glu, and Lys58Glu were selected. These amino acid substitutions were integrated into SpA' (SEQ ID NO:11) to design the protein SpA3b.

(e-2)

After synthesis of a polynucleotide encoding SpA3b designed in (e-1), PCR was used to prepare a polynucleotide containing the nucleotide sequence. The PCR was carried out by the same method as in (a-2) using the synthesized polynucleotide as a template DNA, and oligonucleotides having the nucleotide sequence of SEQ ID NO:25 or SEQ ID NO:27 as PCR primers.

(e-3)

The polynucleotide obtained was purified, and digested with the restriction enzymes NcoI and XhoI, followed by ligation into the expression vector pET-28a that had been preliminarily digested with the restriction enzymes NcoI and XhoI. Using the resulting ligation product, the *Escherichia coli* BL21 (DE3) strain was transformed.

(e-4)

The transformant obtained was cultured in LB medium supplemented with 50 μg/mL kanamycin, and then the expression vector (which was named pET-SpA3b) was extracted using a QIAprep Spin Miniprep kit.

(e-5)

The nucleotide sequence of pET-SpA3b was analyzed by the same method as in Example 1(5). As a result of the sequence analysis, it could be confirmed that the expression vector pET-SpA3b contains a polynucleotide encoding SpA3b inserted therein. The amino acid sequence of SpA3b is shown in SEQ ID NO:21, and the nucleotide sequence encoding SpA3b is shown in SEQ ID NO:22.

Example 5 Evaluation of Alkaline Stabilities of Immunoglobulin-Binding Proteins Having Amino Acid Substitutions (1)

Each transformant that expresses the wild-type immunoglobulin-binding protein prepared in Example 1 (SEQ ID NO:1) or a mutant-type immunoglobulin-binding protein (having amino acid substitutions) prepared in Example 4 (SpA2 (SEQ ID NO:13), SpA3a (SEQ ID NO:15), SpA4a (SEQ ID NO:17), SpA5a (SEQ ID NO:19), or SpA3b (SEQ ID NO:21)) was inoculated to 2 mL of 2× YT liquid medium supplemented with 50 μg/mL kanamycin. Preculture was carried out by aerobically performing shake culture at 37° C. overnight.

(2)

To 20 mL of 2× YT liquid medium supplemented with 50 μg/mL of kanamycin, 200 μL of the preculture liquid was inoculated, and shake culture was aerobically carried out at 37° C.

(3)

Three hours after the beginning of the culture, the culture temperature was changed to 20° C., and IPTG was added to a final concentration of 0.1 mM. Shake culture was then aerobically carried out at 20° C. overnight.

(4)

Thereafter, the cells were collected by centrifugation, and a protein extract was prepared using BugBuster Protein Extraction Reagent (manufactured by Merck).

(5)

The antibody-binding activity of the wild-type immunoglobulin-binding protein (SEQ ID NO:1) or the mutant-type immunoglobulin-binding protein (SEQ ID NO:13, 15, 17, 19, or 21) in the protein extract prepared in (4) was measured using the ELISA method described in Example 3(4).

(6)

The extracts were diluted such that the concentration of each protein became the same using Tris-Buffered Saline (TBS). One half of each protein solution obtained was mixed with an equal volume of 1 M NaOH, and the other half was mixed with an equal volume of TBS. Each mixture was then left to stand at 25° C. for 15 hours.

(7)

After adding 4 volumes of 1 M Tris buffer (pH 7.0) thereto, the antibody-binding activity of each of the alkali-treated protein solution (mixed with 1 M NaOH) and the alkali-untreated protein solution (mixed with TBS) was measured by the ELISA method described in Example 3(4). The antibody-binding activity of the immunoglobulin-binding protein subjected to the alkali treatment was divided by the antibody-binding activity of the immunoglobulin-binding protein without the alkali treatment, to calculate the remaining activity for evaluation of the alkaline stability.

The results are shown in Table 5. All of the mutant-type immunoglobulin-binding proteins evaluated herein (SpA2 (SEQ ID NO:13), SpA3a (SEQ ID NO:15), SpA4a (SEQ ID NO:17), SpA5a (SEQ ID NO:19), and SpA3b (SEQ ID NO:21)) showed higher remaining activities compared to the wild-type immunoglobulin-binding protein (SEQ ID NO:1). Thus, these mutant-type immunoglobulin-binding proteins were found to have improved alkaline stability.

TABLE 5

| Example | Immunoglobulin-binding protein Name | SEQ ID NO: | Remaining activity [%] |
| --- | --- | --- | --- |
| Example 4(a) | SpA2 | 13 | 79 |
| Example 4(b) | SpA3a | 15 | 77 |
| Example 4(c) | SpA4a | 17 | 84 |
| Example 4(d) | SpA5a | 19 | 83 |
| Example 4(e) | SpA3b | 21 | 77 |
| Example 1 | Wild type | 1 | 64 |

Example 6 Introduction of Mutations into Immunoglobulin-Binding Protein Having Improved Alkaline Stability, and Preparation of Library Among the mutant-type immunoglobulin-binding proteins evaluated in Example 5, SpA4a (Example 4(c)) was selected, and mutations were randomly introduced to the polynucleotide portion encoding SpA4a (SEQ ID NO:18) by error-prone PCR.

(1)

Using the expression vector pET-SpA4a prepared in Example 4(c) as a template DNA, error-prone PCR was carried out. For the error-prone PCR, a reaction liquid having the composition shown in Table 2 was prepared, and the reaction liquid was heat-treated at 95° C. for 2 minutes, followed by performing 30 cycles of reaction wherein each cycle included a first step at 95° C. for 30 seconds, a second step at 50° C. for 30 seconds, and a third step at 72° C. for 90 seconds, and then finally performing heat treatment at 72° C. for 7 minutes. By the error-prone PCR, mutations were well introduced into the polynucleotide (SEQ ID NO:18) encoding the mutant-type immunoglobulin-binding protein (SpA4a). The average mutation introduction rate was 1.09%.

(2)

The PCR product obtained was purified, and digested with the restriction enzymes NcoI and XhoI, followed by ligation into the expression vector pET-28a that had been preliminarily digested with the restriction enzymes NcoI and XhoI.

(3)

After completion of the ligation reaction, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a random mutant library Example 7 Screening of Alkali-Stable Immunoglobulin-Binding Proteins (Part 2) (1)

About 1000 strains from the random mutant library (transformants) prepared in Example 6 were each cultured by the method described in Example 3(1) and (2) to allow expression of immunoglobulin-binding protein.

(2)

Thereafter, a culture supernatant containing the immunoglobulin-binding protein was obtained by a centrifugation operation, and diluted 40-fold with pure water. The diluted solution was mixed with an equal amount of 2 M NaOH, and alkali treatment was carried out at 60° C. for 30 minutes. Thereafter, neutralization with 4 volumes of 1 M Tris buffer (pH 7.0) was carried out.

(3)

The antibody-binding activity of the immunoglobulin-binding protein subjected to the alkali treatment and the antibody-binding activity of the immunoglobulin-binding protein without the alkali treatment were measured by the ELISA method described in Example 3(4).

(4)

The antibody-binding activity of the immunoglobulin-binding protein subjected to the alkali treatment was divided by the antibody-binding activity of the immunoglobulin-binding protein without the alkali treatment, to calculate the remaining activity. Transformants showing expression of immunoglobulin-binding proteins having improved alkaline stability (improved remaining activity) compared to SpA4a were selected.

(5)

Each selected transformant was cultured, and an expression vector was prepared therefrom using a QIAprep Spin Miniprep kit (manufactured by QIAGEN).

(6)

The nucleotide sequence of the polynucleotide region encoding the immunoglobulin-binding protein inserted in the expression vector obtained was analyzed by the method described in Example 1(5) to identify the position of amino acid substitution.

For the immunoglobulin-binding protein expressed by each transformant selected in (4), the position of the amino acid substitution in terms of SpA4a (SEQ ID NO:17) and the remaining activity [%] after 15 hours of alkali treatment at 25° C. using 0.5 M NaOH are summarized in Table 6 and Table 7. It can be said that immunoglobulin-binding proteins in which at least any one of the amino acid substitutions Asn3Ile, Asn3Thr, Asn11Lys, Asn11Tyr, and Lys(Glu)58Val (this expression represents the fact that the lysine at position 58 of SEQ ID NO:1 was once substituted to glutamic acid in the preparation of SpA4a, which substitution was further followed by substitution to valine) occurred from the amino acid sequence of SEQ ID NO:17 have improved alkaline stability compared to SpA4a (SEQ ID NO:17).

The amino acid sequence of the protein in which the amino acid substitution $Asn3_{17}Ile$ (this expression represents the fact that the aspartic acid at position 3 of SEQ ID NO:17 is substituted to isoleucine; the same applies hereinafter) occurred (which was named SpA5b) from the amino acid sequence of SEQ ID NO:17 is shown in SEQ ID NO:28; the amino acid sequence of the protein in which the amino acid substitution $Asn3_{17}Thr$ occurred (which was named SpA5c) is shown in SEQ ID NO:29; the amino acid sequence of the protein in which the amino acid substitution $Asn11_{17}Lys$ occurred (which was named SpA5d) is shown in SEQ ID NO:30; the amino acid sequence of the protein in which the amino acid substitution $Asn11_{17}Tyr$ occurred (which was named SpA5e) is shown in SEQ ID NO:31; and the amino acid sequence of the protein in which the amino acid substitution $Lys(Glu)58_{17}Val$ occurred (which was named SpA4b) is shown in SEQ ID NO:32.

TABLE 6

| Immunoglobulin-binding protein | | | |
|---|---|---|---|
| Amino acid substitution | Name | SEQ ID NO: | Remaining activity [%] |
| Asn3Ile | SpA5b | 28 | 84 |
| Asn11Lys | SpA5d | 30 | 89 |
| Asn11Tyr | SpA5e | 31 | 85 |
| — | SpA4a | 17 | 82 |
| — | Wild type | 1 | 69 |

TABLE 7

| Immunoglobulin-binding protein | | | |
|---|---|---|---|
| Amino acid substitution | Name | SEQ ID NO: | Remaining activity [%] |
| Asn3Thr | SpA5c | 29 | 87 |
| Asn11Lys | SpA5d | 30 | 86 |
| Lys(Glu)58Val | SpA4b | 32 | 88 |
| — | SpA4a | 17 | 84 |
| — | Wild type | 1 | 72 |

Example 8 Introduction of Mutations into Immunoglobulin-Binding Protein Having Improved Alkaline Stability, and Preparation of Library Among the mutant-type immunoglobulin-binding proteins evaluated in Example 7, SpA5d (Example 6) was selected, and mutations were randomly introduced to the polynucleotide portion encoding SpA5d (SEQ ID NO:33) by error-prone PCR.

(1)
Error-prone PCR was carried out using, as a template DNA, the expression vector of SpA5d, which was obtained from the random mutant library prepared in Example 6. For the error-prone PCR, a reaction liquid having the composition shown in Table 2 was prepared, and the reaction liquid was heat-treated at 95° C. for 2 minutes, followed by performing 30 cycles of reaction wherein each cycle included a first step at 95° C. for 30 seconds, a second step at 50° C. for 30 seconds, and a third step at 72° C. for 90 seconds, and then finally performing heat treatment at 72° C. for 7 minutes. By the error-prone PCR, mutations were well introduced into the polynucleotide (SEQ ID NO:33) encoding the mutant-type immunoglobulin-binding protein (SpA5d). The average mutation introduction rate was 0.92%.

(2)
The PCR product obtained was purified, and digested with the restriction enzymes NcoI and XhoI, followed by ligation into the expression vector pET-28a that had been preliminarily digested with the restriction enzymes NcoI and XhoI.

(3)
After completion of the ligation reaction, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a random mutant library Example 9 Screening of Alkali-Stable Immunoglobulin-Binding Proteins (Part 3)

(1)
About 1000 strains from the random mutant library (transformants) prepared in Example 8 were each cultured by the method described in Example 3(1) and (2) to allow expression of immunoglobulin-binding protein.

(2)
Thereafter, a culture supernatant containing the immunoglobulin-binding protein was obtained by a centrifugation operation, and diluted 40-fold with pure water. The diluted solution was mixed with an equal amount of 2 M NaOH, and alkali treatment was carried out at 62° C. for 30 minutes. Thereafter, neutralization with 4 volumes of 1 M Tris buffer (pH 7.0) was carried out.

(3)
The antibody-binding activity of the immunoglobulin-binding protein subjected to the alkali treatment and the antibody-binding activity of the immunoglobulin-binding protein without the alkali treatment were measured by the ELISA method described in Example 3(4).

(4)
The antibody-binding activity of the immunoglobulin-binding protein subjected to the alkali treatment was divided by the antibody-binding activity of the immunoglobulin-binding protein without the alkali treatment, to calculate the remaining activity. Transformants showing expression of immunoglobulin-binding proteins having improved alkaline stability (improved remaining activity) compared to SpA5d were selected.

(5)
Each selected transformant was cultured, and an expression vector was prepared therefrom using a QIAprep Spin Miniprep kit (manufactured by QIAGEN).

(6)

The nucleotide sequence of the polynucleotide region encoding the immunoglobulin-binding protein inserted in the expression vector obtained was analyzed by the method described in Example 1(5) to identify the position of amino acid substitution.

For the immunoglobulin-binding protein expressed by each transformant selected in (4), the position of the amino acid substitution in terms of SpA5d (SEQ ID NO:30) and the remaining activity [%] after 15 hours of alkali treatment at 25° C. using 0.5 M NaOH are summarized in Table 8. It can be said that immunoglobulin-binding proteins in which at least any one of the amino acid substitutions Glu15Ala and Lys(Glu)58Gly occurred from the amino acid sequence of SEQ ID NO:30 have improved alkaline stability compared to SpA5d (SEQ ID NO:30).

The amino acid sequence of the protein in which the amino acid substitution $Glu15_{30}Ala$ (this expression represents the fact that the glutamic acid at position 15 of SEQ ID NO:30 is substituted to alanine; the same applies hereinafter) occurred (which was named SpA6a) from the amino acid sequence of SEQ ID NO:30 is shown in SEQ ID NO:34; and the amino acid sequence of the protein in which the amino acid substitution $Lys(Glu)58_{30}Gly$ occurred (which was named SpA5f) is shown in SEQ ID NO:35.

TABLE 8

| Immunoglobulin-binding protein | | | |
|---|---|---|---|
| Amino acid substitution | Name | SEQ ID NO: | Remaining activity [%] |
| Glu15Ala | SpA6a | 34 | 91 |
| Lys(Glu)58Gly | SpA5f | 35 | 90 |
| — | SpA5d | 30 | 88 |

Example 10 Introduction of Mutations into Immunoglobulin-Binding Protein Having Improved Alkaline Stability, and Preparation of Library Among the mutant-type immunoglobulin-binding proteins evaluated in Example 9, SpA6a (Example 8) was selected, and mutations were randomly introduced to the polynucleotide portion encoding SpA6a (SEQ ID NO:36) by error-prone PCR.

(1)

Error-prone PCR was carried out using, as a template DNA, the expression vector of SpA6a, which was obtained from the random mutant library prepared in Example 8. For the error-prone PCR, a reaction liquid having the composition shown in Table 2, 9, or 10 was prepared, and the reaction liquid was heat-treated at 95° C. for 2 minutes, followed by performing 30 cycles of reaction wherein each cycle included a first step at 95° C. for 30 seconds, a second step at 50° C. for 30 seconds, and a third step at 72° C. for 90 seconds, and then finally performing heat treatment at 72° C. for 7 minutes. By the error-prone PCR, mutations were well introduced into the polynucleotide (SEQ ID NO:36) encoding the mutant-type immunoglobulin-binding protein (SpA6a). The average mutation introduction rate was 1.03% in the case where the PCR was carried out using the conditions (composition) shown in Table 2, 1.44% in the case where the PCR was carried out using the conditions (composition) shown in Table 9, and 2.87% in the case where the PCR was carried out using the conditions (composition) shown in Table 10.

TABLE 9

| Composition | Volume |
|---|---|
| Template DNA(10 ng/μL) | 1 μL |
| PCR primer(SEQ ID NO: 6)(10 μM) | 4 μL |
| PCR primer(SEQ ID NO: 7)(10 μM) | 4 μL |
| 25 mM MgCl$_2$ | 12 μL |
| 2.5 mM dNTP mixture | 8 μL |
| 10 mM MnCl$_2$ | 4 μL |
| 10 × Ex Taq buffer(Takara Bio Inc.) | 10 μL |
| GoTaq DNA polymerase(Promega KK) | 1 μL |
| H$_2$O | up to 100 μL |

TABLE 10

| Composition | Volume |
|---|---|
| Template DNA(10 ng/μL) | 1 μL |
| PCR primer(SEQ ID NO: 6)(10 μM) | 4 μL |
| PCR primer(SEQ ID NO: 7)(10 μM) | 4 μL |
| 25 mM MgCl$_2$ | 12 μL |
| 2.5 mM dNTP mixture | 8 μL |
| 10 mM MnCl$_2$ | 5 μL |
| 10 × Ex Taq buffer(Takara Bio Inc.) | 10 μL |
| GoTaq DNA polymerase(Promega KK) | 1 μL |
| H$_2$O | up to 100 μL |

(2)

The PCR product obtained was purified, and digested with the restriction enzymes NcoI and XhoI, followed by ligation into the expression vector pET-28a that had been preliminarily digested with the restriction enzymes NcoI and XhoI.

(3)

After completion of the ligation reaction, the *Escherichia coli* BL21 (DE3) strain was transformed using the reaction liquid, and then cultured (37° C., 16 hours) on LB plate medium supplemented with 50 μg/mL kanamycin. The resulting colonies, formed on the plate, were provided as a random mutant library.

Example 11 Screening of Alkali-Stable Immunoglobulin-Binding Proteins (Part 4)

(1)

About 2500 strains from the random mutant libraries (transformants) prepared in Example 10 (about 1000 strains from the library obtained using the conditions of Table 2, about 1000 strains from the library obtained using the conditions of Table 9, and about 500 strains from the library obtained using the conditions of Table 10) were each cultured by the method described in Example 3(1) and (2) to allow expression of immunoglobulin-binding protein.

(2)

Thereafter, a culture supernatant containing the immunoglobulin-binding protein was obtained by a centrifugation operation, and diluted 40-fold with pure water. The diluted solution was mixed with an equal amount of 2 M NaOH, and alkali treatment was carried out at 65 to 68° C. for 30 minutes. Thereafter, neutralization with 4 volumes of 1 M Tris buffer (pH 7.0) was carried out.

(3)

The antibody-binding activity of the immunoglobulin-binding protein subjected to the alkali treatment and the antibody-binding activity of the immunoglobulin-binding protein without the alkali treatment were measured by the ELISA method described in Example 3(4).

(4)

The antibody-binding activity of the immunoglobulin-binding protein subjected to the alkali treatment was divided by the antibody-binding activity of the immunoglobulin-binding protein without the alkali treatment, to calculate the remaining activity. Transformants showing expression of immunoglobulin-binding proteins having improved alkaline stability (improved remaining activity) compared to SpA6a were selected.

(5)

Each selected transformant was cultured, and an expression vector was prepared therefrom using a QIAprep Spin Miniprep kit (manufactured by QIAGEN).

(6)

The nucleotide sequence of the polynucleotide region encoding the immunoglobulin-binding protein inserted in the expression vector obtained was analyzed by the method described in Example 1(5) to identify the position of amino acid substitution.

For the immunoglobulin-binding protein expressed by each transformant selected in (4), the position of the amino acid substitution in terms of SpA6a (SEQ ID NO:34) and the remaining activity [%] after 15 hours of alkali treatment at 25° C. using 0.5 M NaOH are summarized in Table 11, Table 12 and Table 13. It can be said that immunoglobulin-binding proteins in which at least any one of the amino acid substitutions Val40Ala, Asn3Ile, Lys(Glu)58Asp, and Lys(Glu)58Val occurred from the amino acid sequence of SEQ ID NO:34 have improved alkaline stability compared to SpA6a (SEQ ID NO:34).

The amino acid sequence of the protein in which the amino acid substitution Val40$_{34}$Ala (this expression represents the fact that the valine at position 40 of SEQ ID NO:34 is substituted to alanine; the same applies hereinafter) occurred (which was named SpA7a) from the amino acid sequence of SEQ ID NO:34 is shown in SEQ ID NO:37; the amino acid sequence of the protein in which the amino acid substitution Asn3$_{34}$Ile occurred (which was named SpA7b) is shown in SEQ ID NO:38; the amino acid sequence of the protein in which the amino acid substitution Lys(Glu)58$_{34}$Asp occurred (which was named SpA6b) is shown in SEQ ID NO:39; and the amino acid sequence of the protein in which the amino acid substitution Lys(Glu)58$_{34}$Val occurred (which was named SpA6c) is shown in SEQ ID NO:40.

TABLE 11

| Immunoglobulin-binding protein | | | |
|---|---|---|---|
| Amino acid substitution | Name | SEQ ID NO: | Remaining activity [%] |
| Val40Ala | SpA7a | 37 | 89 |
| — | SpA6a | 34 | 86 |

TABLE 12

| Immunoglobulin-binding protein | | | |
|---|---|---|---|
| Amino acid substitution | Name | SEQ ID NO: | Remaining activity [%] |
| Asn3Ile | SpA7b | 38 | 88 |
| — | SpA6a | 34 | 83 |

TABLE 13

| Immunoglobulin-binding protein | | | |
|---|---|---|---|
| Amino acid substitution | Name | SEQ ID NO: | Remaining activity [%] |
| Lys(Glu)58Asp | SpA6b | 39 | 87 |
| Lys(Glu)58Val | SpA6c | 40 | 87 |
| — | SpA6a | 34 | 83 |

INDUSTRIAL APPLICABILITY

The immunoglobulin-binding protein of the present invention is a protein containing an amino acid sequence provided by substituting an amino acid residue(s) at a particular position(s) in an immunoglobulin-binding domain such as domain C of protein A derived from a bacterium belonging to the genus *Staphylococcus*, to another/other particular amino acid residue(s). The immunoglobulin-binding protein of the present invention has improved stability against alkali, and is useful as a ligand protein for an adsorbent for separation of an antibody (immunoglobulin).

The invention claimed is:

1. An immunoglobulin-binding protein, which is a protein of the following (a), (b), (c), or (d):

(a) a protein containing an amino acid sequence which is the same as the amino acid sequence of SEQ ID NO:1 except that the amino acid sequence of the protein has the at least one amino acid substitution selected from the following (1) to (3), (5), (6), and (8):
  (1) substitution of the amino acid residue corresponding to the aspartic acid at position 2 of SEQ ID NO:1 to glutamic acid;
  (2) substitution of the amino acid residue corresponding to the lysine at position 49 of SEQ ID NO:1 to methionine;
  (3) substitution of the amino acid residue corresponding to the asparagine at position 21 of SEQ ID NO:1 to tyrosine;
  (5) substitution of the amino acid residue corresponding to the asparagine at position 3 of SEQ ID NO:1 to isoleucine or threonine;
  (6) substitution of the amino acid residue corresponding to the asparagine at position 11 of SEQ ID NO:1 to lysine or tyrosine;
  (8) substitution of the amino acid residue corresponding to the valine at position 40 of SEQ ID NO:1 to alanine;

(b) a protein containing an amino acid sequence which is the same as the amino acid sequence of SEQ ID NO:1 except that the amino acid sequence of the protein has the at least one amino acid substitution selected from the following (1) to (3), (5), (6), and (8), and also has substitution, deletion, insertion, and/or addition of one or several amino acid residues at one or several positions other than the position(s) of the at least one amino acid substitution, the protein having immunoglobulin-binding activity:
  (1) substitution of the amino acid residue corresponding to the aspartic acid at position 2 of SEQ ID NO:1 to glutamic acid;
  (2) substitution of the amino acid residue corresponding to the lysine at position 49 of SEQ ID NO:1 to methionine;
  (3) substitution of the amino acid residue corresponding to the asparagine at position 21 of SEQ ID NO:1 to tyrosine;
  (5) substitution of the amino acid residue corresponding to the asparagine at position 3 of SEQ ID NO:1 to isoleucine or threonine;
  (6) substitution of the amino acid residue corresponding to the asparagine at position 11 of SEQ ID NO:1 to lysine or tyrosine;
  (8) substitution of the amino acid residue corresponding to the valine at position 40 of SEQ ID NO:1 to alanine; or (c) a protein containing an amino acid sequence having a homology of not less than 70% with respect to the entire sequence of an amino acid sequence which is the same as the amino acid sequence of SEQ ID NO:1 except for the at least one amino acid substitution selected from the following (1) to (3), (5), (6), and (8), wherein the amino acid sequence of the protein retains the at least one amino acid substitution, the protein having immunoglobulin-binding activity:
  (1) substitution of the amino acid residue corresponding to the aspartic acid at position 2 of SEQ ID NO:1 to glutamic acid;
  (2) substitution of the amino acid residue corresponding to the lysine at position 49 of SEQ ID NO:1 to methionine;
  (3) substitution of the amino acid residue corresponding to the asparagine at position 21 of SEQ ID NO:1 to tyrosine;
  (5) substitution of the amino acid residue corresponding to the asparagine at position 3 of SEQ ID NO:1 to isoleucine or threonine;
  (6) substitution of the amino acid residue corresponding to the asparagine at position 11 of SEQ ID NO:1 to lysine or tyrosine;
  (8) substitution of the amino acid residue corresponding to the valine at position 40 of SEQ ID NO:1 to alanine (d) a protein containing an amino acid sequence which is the same as the amino acid sequence of the protein recited in (a), (b), or (c) except that the amino acid sequence of the protein further has at least one amino acid substitution selected from the following (4), (7), and (9) to (13):
  (4) substitution of the amino acid residue corresponding to the lysine at position 58 of SEQ ID NO:1 to glutamic acid, valine, glycine, or aspartic acid;

(7) substitution of the amino acid residue corresponding to the glutamic acid at position 15 of SEQ ID NO:1 to alanine;
(9) substitution of the amino acid residue corresponding to the glycine at position 29 of SEQ ID NO:1 to alanine;
(10) substitution of the amino acid residue corresponding to the lysine at position 4 of SEQ ID NO:1 to arginine;
(11) substitution of the amino acid residue corresponding to the lysine at position 7 of SEQ ID NO:1 to glutamic acid;
(12) substitution of the amino acid residue corresponding to the asparagine at position 6 of SEQ ID NO:1 to aspartic acid; and
(13) substitution of the amino acid residue corresponding to the lysine at position 42 of SEQ ID NO:1 to arginine.

2. The immunoglobulin-binding protein according to claim 1, comprising an amino acid sequence which is the same as the amino acid sequence of SEQ ID NO:1 except that the amino acid sequence of the immunoglobulin-binding protein has at least the amino acid substitution(s) presented in the following (3-1) and (4-1):
(3-1) substitution of the asparagine at position 21 of SEQ ID NO:1 to tyrosine; and
(4-1) substitution of the lysine at position 58 of SEQ ID NO:1 to glutamic acid.

3. The immunoglobulin-binding protein according to claim 1, comprising the amino acid sequence of any of SEQ ID NOs:8, 13, 15, 17, and 19.

4. The immunoglobulin-binding protein according to claim 1, comprising an amino acid sequence which is the same as the amino acid sequence of SEQ ID NO:17 except that the amino acid sequence of the immunoglobulin-binding protein has at least one amino acid substitution selected from the following (I) to (V):
(I) substitution of the asparagine at position 3 of SEQ ID NO:17 to isoleucine or threonine;
(II) substitution of the asparagine at position 11 of SEQ ID NO:17 to lysine or tyrosine;
(III) substitution of the glutamic acid at position 58 of SEQ ID NO:17 to valine, glycine, or aspartic acid;
(IV) substitution of the glutamic acid at position 15 of SEQ ID NO:17 to alanine; and
(V) substitution of the valine at position 40 of SEQ ID NO:17 to alanine.

5. The immunoglobulin-binding protein according to claim 4, comprising the amino acid sequence of any of SEQ ID NOs:28 to 32, 34, 35, and 37 to 40.

6. The immunoglobulin-binding protein according to claim 1, comprising an amino acid sequence which is the same as the amino acid sequence of SEQ ID NO:1 except that the amino acid sequence of the immunoglobulin-binding protein has at least the amino acid substitution presented in the following (2-1):
(2-1) substitution of the lysine at position 49 of SEQ ID NO:1 to methionine.

7. A polynucleotide encoding the immunoglobulin-binding protein according to claim 1.

8. An expression vector comprising the polynucleotide according to claim 7.

9. A transformant comprising the polynucleotide according to claim 7.

10. The transformant according to claim 9, which is *Escherichia coli*.

11. A method of producing an immunoglobulin-binding protein, the method comprising:
culturing a transformant comprising a polynucleotide encoding the immunoglobulin-binding protein according to claim 1, to allow expression of the immunoglobulin-binding protein according to claim 1; and
recovering the expressed protein.

12. An immunoglobulin adsorbent comprising:
an insoluble support; and
the immunoglobulin-binding protein according to claim 1 immobilized on the insoluble support.

13. A method of separating immunoglobulin, the method comprising:
applying a solution containing immunoglobulin to a column packed with the adsorbent according to claim 12, to allow adsorption of the immunoglobulin to the adsorbent; and
eluting the immunoglobulin that has adsorbed to the adsorbent.

* * * * *